(12) United States Patent
Yun et al.

(10) Patent No.: US 9,567,614 B2
(45) Date of Patent: Feb. 14, 2017

(54) GENETICALLY ENGINEERED BACTERIAL CELL HAVING ENHANCED ACTIVITY OF GLND OR GLNK AND METHOD OF PRODUCING ORGANIC ACID BY USING THE SAME

(71) Applicant: Samsung Electronics Co., Ltd., Suwon-si, Gyeonggi-do (KR)

(72) Inventors: Jiae Yun, Hwaseong-si (KR); Jieun Kim, Suwon-si (KR); Soonchun Chung, Seoul (KR); Joonsong Park, Seoul (KR); Jinhwan Park, Suwon-si (KR); Wooyong Lee, Hwaseong-si (KR); Kwangmyung Cho, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/673,004

(22) Filed: Mar. 30, 2015

(65) Prior Publication Data
US 2015/0275239 A1 Oct. 1, 2015

(30) Foreign Application Priority Data
Mar. 28, 2014 (KR) .................. 10-2014-0037048

(51) Int. Cl.
| | | |
|---|---|---|
| C12P 7/46 | (2006.01) | |
| C12N 9/12 | (2006.01) | |
| C07K 14/34 | (2006.01) | |
| C12P 7/40 | (2006.01) | |

(52) U.S. Cl.
CPC .................. *C12P 7/40* (2013.01); *C07K 14/34* (2013.01); *C12N 9/1241* (2013.01); *C12P 7/46* (2013.01); *C12Y 207/07059* (2013.01)

(58) Field of Classification Search
None
See application file for complete search history.

(56) References Cited

U.S. PATENT DOCUMENTS

| 7,368,268 B2 | 5/2008 | Murakami et al. | |
|---|---|---|---|
| 7,763,447 B2 | 7/2010 | Murase et al. | |
| 2005/0079588 A1* | 4/2005 | Sindelar | C12P 13/08 435/115 |

FOREIGN PATENT DOCUMENTS

| JP | 2006-000091 B2 | 1/2006 |
|---|---|---|
| KR | 2006-0011345 A | 2/2006 |

OTHER PUBLICATIONS

Nolden et al., Sensing nitrogen limitation in Corynebacterium glutamicum: the role of gInK and gInD, Mol. Microbiol., 2001, 42, 1281-95.*
GenBank, Accession No. AJ010319.1, 2005, www.ncbi.nlm.nih.gov.*
Rehm et al., Engineering of nitrogen metabolism and its regulation in Corynebacterium glutamicum: influence on amino acid pools and production, Appl. Microbiol. Biotechnol., Oct. 2010, 89, 239-48.*
Muller et al., "Mutation-induced metabolite pool alterations in *Corynebacterium glutamicum:* Towards the identification of nitrogen control signals", *Journal of Biotechnology,* 126:440-453 (2006).

* cited by examiner

*Primary Examiner* — Robert Mondesi
*Assistant Examiner* — Todd M Epstein
(74) *Attorney, Agent, or Firm* — Leydig, Voit & Mayer, Ltd.

(57) ABSTRACT

A genetically engineered bacteria cell having an enhanced activity of GlnD or GlnK, and a method of producing succinic acid by using the genetically engineered bacteria cell are provided.

13 Claims, 2 Drawing Sheets

GENETICALLY ENGINEERED BACTERIAL CELL HAVING ENHANCED ACTIVITY OF GLND OR GLNK AND METHOD OF PRODUCING ORGANIC ACID BY USING THE SAME

RELATED APPLICATIONS

This application claims the benefit of Korean Patent Application No. 10-2014-0037048, filed on Mar. 28, 2014, in the Korean Intellectual Property Office, the disclosure of which is incorporated herein in its entirety by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 51,917 bytes ASCII (Text) file named "719078_ST25.TXT," created Feb. 27, 2015.

BACKGROUND

1. Field

The present disclosure relates to genetically engineered bacteria cells having an enhanced activity of GlnD or GlnK, and methods of producing succinic acid by using the genetically engineered bacteria cells.

2. Description of the Related Art

*Corynebacterium* genus microorganisms as a class of gram-negative strains are widely in use for the production of amino acids such as glutamate, lysine, and threonine. *Corynebacterium glutamicum* is advantageous for use as an industrial strain due to simple growth conditions, a stable genome structure, and no environmental damage. *Corynebacterium glutamicum* is an aerobic bacterium, which stops metabolic processes except for basal metabolic process for energy generation when its oxygen supply is interrupted or under oxygen-deficient conditions thereby resulting in the production of lactic acid, acetic acid, succinic acid, and the like for energy generation.

Tricarboxylic acid (TCA) cycle is a metabolic pathway to generate energy and intermediate metabolites in biological species. The intermediate metabolites of the TCA cycles are used to synthesize useful chemical materials via other metabolic processes. Succinic acid is dicarboxylic acid used as a source material for biodegradable polymers, medicines, and cosmetics. Most industrially available succinic acids are synthesized from n-butane and acetylate originating from crude oil or liquefied natural gas. Only a small amount of succinic acid for use in special purposes such as for medicines or foods is produced via fermentation using microorganisms.

In general, chemical synthetic processes may require depletable fossil sources as basic materials and produce a large quantity of harmful byproducts. Therefore, there is a need for microorganisms capable of efficiently producing succinic acid, even by conventional methods, or a method of producing such microorganisms to overcome the significant drawbacks of conventional chemical synthetic processes.

SUMMARY

Provided is a genetically engineered bacteria cell having an enhanced ability to produce an organic acid, wherein the genetically engineered bacteria cell comprises a genetic modification that increases the activity of GlnK; GlnD; a protein having a sequence identity of about 95% or more to SEQ ID NO: 1 or 2; or combination thereof, as compared to a parent cell, wherein the genetically engineered bacteria cell exhibits increased organic acid production compared to a parent cell.

Also provided is a method of producing an organic acid by using the genetically engineered bacteria cell. The method comprises culturing the genetically modified bacteria cell and recovering the organic acid from the culture.

Further provided is a method of producing the genetically engineered bacteria cell by introducing a genetic modification that increases the activity of GlnK; GlnD; a protein having a sequence identity of about 95% or more to SEQ ID NO: 1 or 2; or combination thereof in a bacteria cell, such as by increasing the copy number of a nucleic acid encoding the one or more proteins, or by enhancing expression of such a nucleic acid through modification of a regulatory element.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
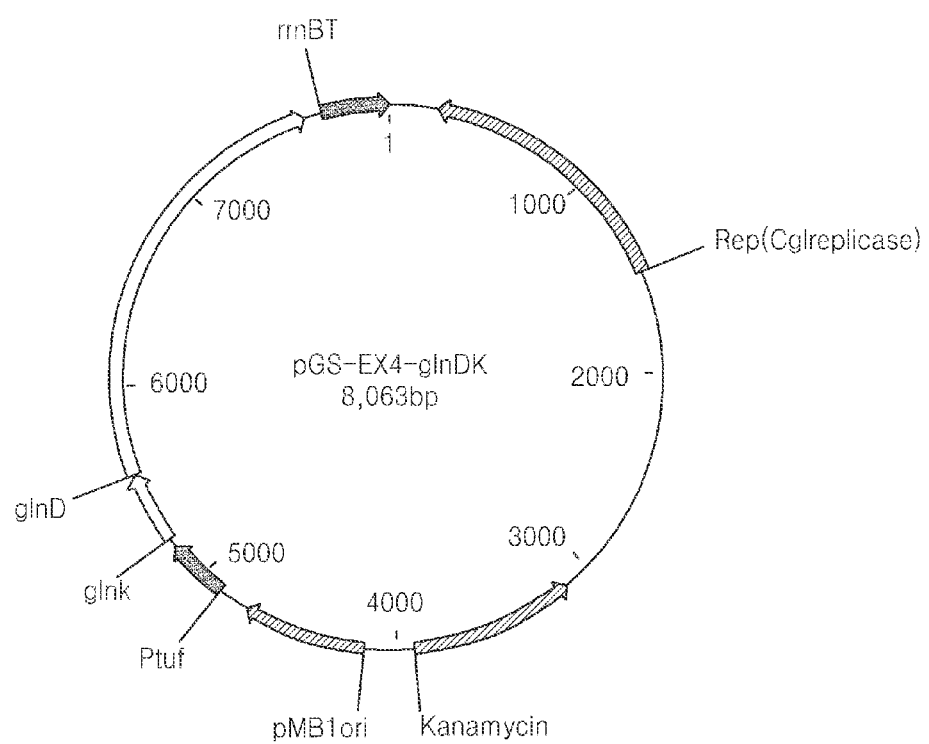
FIG. 1 is a cleavage map of a pGS-EX4-glnDK vector.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

As used herein, the expression "increase in activity" or "increased activity" of a protein or an enzyme may refer to a sufficient increase in the amount thereof or the activity thereof, and may also refer to an activity level of a cell, an isolated protein, or isolated enzyme that is higher than that of a comparative cell of the same type (i.e., a parent cell) or an original protein or original enzyme produced by a parent cell. In other words, the activity of a protein or enzyme may be increased by about 5% or more, about 10% or more, about 15% or more, about 20% or more, about 30% or more, about 50% or more, about 60% or more, about 70% or more, or about 100% than the activity of a non-engineered protein or enzyme, i.e., a wild-type or parent protein or enzyme. The activity of a specific protein or enzyme in a cell may be increased by about 5% or more, about 10% or more, about 15% or more, about 20% or more, about 30% or more, about 50% or more, about 60% or more, about 70% or more, or about 100% than the activity of the same protein or enzyme in a non-engineered cell, i.e., a parent cell. The cell with the increased activity of a protein or an enzyme may be identified by using a method known in the art. The cell with the increased activity of a protein or an enzyme may be identified by using identifying the expression level of the gene encoding the protein or the enzyme, for example, PCR, and RT-PCR using primers specific to the gene, or ELISA, and western blotting using antibodies specific to the protein or enzyme.

The increased activity of the protein or enzyme may occur by increasing the expression or specific activity of the protein or enzyme. The increased expression may occur by introducing a polynucleotide encoding the protein or enzyme into a cell, increasing a copy number of the polynucleotide in the cell, or mutating a regulatory region of the polynucleotide. The polynucleotide that is externally introduced or the one of which copy number is increased may be an endogenous gene or an exogenous gene. The endogenous gene refers to a gene that is present in a genetic material of a microorganism. The exogenous gene refers to a gene that is externally introduced into a cell, and may be, for example, homologous or heterologous with respect to a host cell into which the gene is introduced.

As used herein, the term "genetic modification" may refer to introduction of a polynucleotide encoding a polypeptide (i.e., an increase in a copy number of the gene), or substitution, addition, insertion, or deletion of at least one nucleotide with a genetic material of a parent cell, or chemical mutation of a genetic material of a parent cell. In other words, genetic modification may include cases associated with a coding region of a polypeptide or a functional fragment thereof of a polypeptide that is heterologous, homologous, or both heterologous and homologous with a referenced species. Genetic modification may also refer to modification in non-coding regulatory regions that are capable of modifying expression of a gene or an operon, wherein the non-coding regulatory regions include a 5'-non coding sequence and/or a 3'-non coding sequence.

The expression "increased copy number" or "copy number increase" may refer to a copy number increase by an introduction or amplification of the gene or may also include a copy number increase by genetically manipulating a cell to have a gene that is not inherently present in the cell. The introduction of the gene may occur by using a vehicle such as a vector. The introduction may be a transient introduction in which the gene is not integrated into the genome, or may be integrated into the genome. The introduction may, for example, occur by introducing a vector into which a polynucleotide encoding a target polypeptide is introduced into the cell and then replicating the vector in the cell or integrating the polynucleotide into the genome of the cell and then replicating the polynucleotide together with the replication of the genome.

The term "gene" as used herein refers to a nucleic acid fragment that may produce an expressed product, for example, mRNA or a protein, via at least one of transcription and translation, and may include a regulatory sequence such as a coding region, for example, a 5'-non-coding sequence, and a 3'-non-coding sequence as well as a non-coding region.

The term "heterologous" as used herein refers to foreign matter that is not native to the cell.

The terms "cell", the "strain", or the "microorganism" as used herein may be interchangeably used, and may include bacteria, yeast, fungi or the like.

The expression "decreased activity" or "decrease in activity" of a protein or enzyme may occur by deletion or disruption of a gene encoding the protein or enzyme. The expression "deletion" or "disruption" of a gene as used herein refers to mutation of part or all of the gene, or part or all of a regulatory sequence of the gene, such as a promoter or a terminator region thereof, such that the gene may be not or less expressed or may show no activity or reduced activity of the enzyme even when the gene is expressed. The mutation may include addition, substitution, insertion, or conversion of at least one nucleotide of the gene. The deletion or disruption of a gene may be achieved by genetic manipulation such as homologous recombination, target directed mutagenesis, or molecular evolution. When a cell includes a plurality of the same genes, or two or more different paralogs, one or more of the genes may be removed or disrupted.

A sequence identity of nucleic acid or polypeptide, according to an embodiment of the present invention, refers to the extent of identity between bases or amino acid residues of sequences obtained after the sequences are aligned so as to best match in certain comparable regions. The sequence identity is a value obtained by comparison of two sequences in certain comparable regions via optimal alignment of the two sequences, wherein portions of the sequences in the certain comparable regions may be added or deleted compared to reference sequences. A percentage of sequence identity may be calculated by, for example, comparing two optimally aligned sequences in the entire comparable regions, determining the number of locations in which the same amino acids or nucleic acids appear to obtain the number of matching locations, dividing the number of the matching locations by the total number of locations in the comparable regions (that is, the size of a range), and multiplying the result of the division by 100 to obtain the percentage of the sequence identity. The percentage of the sequence identity may be determined using a known sequence comparison program, for example, BLASTN, BLASTP (NCBI), CLC Main Workbench (CLC bio), and MegAlign™ (DNASTAR Inc.).

Various levels of sequence identity may be used to identify various types of polypeptides or polynucleotides having the same or similar functions. For example, a sequence identity of about 50% or more, about 55% or more, about 60% or more, about 65% or more, about 70% or more, about 75% or more, about 80% or more, about 85% or more, about 90% or more, about 95% or more, about 96% or more, about 97% or more, about 98% or more, about 99% or more, or 100% may be used.

As used herein, "GlnK" denotes a protein encoded by a glnK gene. GlnK may be a $P_{II}$-type signal transfer protein. As used herein, "GlnD" denotes a protein encoded by a glnD gene. The GlnD protein may induce adenylation and/or deadenylation of GlnK or uridylation and/or deuridylation of GlnK. For example, the GlnD protein may induce adenylation and/or deadenylation of GlnK in Corynebacterium genus bacteria, for example, C. glutamicum, and may induce uridylation and/or deuridylation of GlnK in Escherichia genus bacteria, for example, Escherichia coli. The GlnD protein may be an adenylyl transferase and/or an uridylyl transferase. The GlnK and GlnD are known as core components of a nitrogen regulatory system in Corynebacterium glutamicum. The glnK and glnD genes may constitute a regulon, and thus may be co-regulated by a regulatory element.

The term "non-engineered cell" as used herein refers to a cell that is not genetically engineered to increase the activity of a protein having a sequence identity of about 95% or more to at least one selected from the group consisting of GlnK and GlnD and/or a cell that is not genetically engineered to have an enhanced ability to produce an organic acid. The term "genetical engineering" refers to artificially changing the composition or structure of a genetic material. A non-engineered cell may be a parent strain used to genetically engineer a bacteria cell to have an increased activity of a protein having a sequence identity of about 95% or more to at least one selected from the group consisting of GlnK and GlnD and/or genetically engineered to have an enhanced ability to produce an organic acid.

The term "organic acid" as used herein is construed as including an organic acid itself, an anion, a salt, a solvate, and a polymorph thereof, and a combination thereof. The salt may be an inorganic acid salt, an organic acid salt, or a metal salt. For example, the inorganic acid salt may be hydrochloride salt, bromate salt, phosphate salt, sulfate salt, or disulfate salt. For example, the organic acid salt may be formate salt, acetate salt, acetate salt, propionate salt, lactate salt, oxalate salt, tartrate salt, malate salt, maleate salt, citrate salt, fumarate salt, besylate salt, camsylate salt, edysilate salt, trifluoroacetate salt, benzoate salt, gluconate salt, methanesulfonate salt, glycolate salt, succinate salt, 4-toluene sulfonate salt, galacturonate salt, embonate salt, glutamate salt, or aspartate salt. For example, the metal salt may be a calcium salt, a sodium salt, a magnesium salt, a strontium salt, or a potassium salt.

According to an embodiment, provided is a genetically engineered bacteria cell having an enhanced ability to produce an organic acid, and in which the activity of a protein having a sequence identity of about 95% or more to at least one selected from the group consisting of GlnK and GlnD is increased compared to a non-engineered cell, i.e., a parent cell.

The organic acid may be a C1-C20 organic acid. For example, the organic acid may be acetic acid, lactic acid, propionic acid, 3-hydroxypropionic acid, butyric acid, 4-hydroxybutyric acid, succinic acid, fumaric acid, malic acid, oxalic acid, adipic acid, or a combination thereof. The organic acid may be a C3-C20 dicarboxylic acid. For example, the organic acid may be a C3-C20 dicarboxylic acid, and in some embodiments, a C3-C5 dicarboxylic acid, or a C4 dicarboxylic acid.

The GlnK and GlnD may have an amino acid sequence of SEQ ID NO: 1 and SEQ ID NO: 2, respectively, or a sequence with a sequence identity of about 95% or more to SEQ ID NO: 1 or SEQ ID NO: 2, respectively.

The GlnK and GlnD may be encoded by a nucleic acid with a sequence of SEQ ID NO: 3 and SEQ ID NO: 4, respectively, or a nucleic acid with a sequence identity of about 95% or more to the nucleotide sequences of SEQ ID NO: 3 and SEQ ID NO: 4, respectively.

The GlnK and GlnD may be encoded by a glnK gene (NCgl1982) and a glnD gene (NCgl1981), respectively.

The genetically engineered bacteria cell may have an ability to produce succinic acid under microaerobic or anaerobic conditions. The microaerobic conditions may refer to incubation conditions for the dissolution of a low level of oxygen in a culture medium. The low level of oxygen may refer to a level of oxygen less than the level of atmospheric oxygen. For example, a low level of oxygen that is about 0.1% to about 10%, about 1% to about 9%, about 2% to about 8%, about 3% or 7%, or about 4% to about 6% of the level of atmospheric oxygen may be allowed to contact a culture medium.

The genetically engineered bacteria cell may belong to the Corynebacterium genus, the Bacillus genus, the Rhizobium genus, the Escherichia genus, the Lactobacillus genus, the Actinobacillus genus, or a combination thereof. The genetically engineered bacteria cell may belong to the Corynebacterium genus, for example, may be Corynebacterium glutamicum, Corynebacterium thermoaminogenes, Brevibacterium flavum, or Brevibacterium lactofermentum. The Corynebacterium glutamicum may be a Corynebacterium glutamicum ATCC13032, S003, or S006 strain.

The increased activity of the protein having a sequence identity of about 95% or more to the at least one of GlnK and GlnD may occur by increase of a copy number of a gene encoding the at least one of GlnK and GlnD or by modification of an expression regulatory sequence of the gene.

The increase in a copy number may be obtained by intracellular introduction of an exogenous gene from outside the cell, or by amplification of an endogenous gene. The amplification of an endogenous gene may include incubating the cell under selection pressure beneficial for the cell. For example, the gene to be amplified in the cell may be fused to a selection marker, for example, antibiotic resistant gene encoding an enzyme degrading the antibiotic, and the gene may be amplified by incubating the cell under the antibiotic.

The introduction of the gene may be implemented via a vehicle, for example, a vector. The introduction may be a transient introduction in which the gene is not integrated into a genome, or may be integrated into a genome. The introduction may be implemented, for example, by introducing a vector into which the gene is introduced into the cell, and then replicating the vector in the cell or integrating the gene into the genome of the cell. The gene may be operably linked to a regulatory sequence that is involved in the regulation of the expression thereof. The regulatory sequence may include a promoter, a 5'-non-coding sequence, a 3'-non-coding sequence, a transcription terminator sequence, an enhancer, or a combination thereof. The gene may be an endogenous gene or an exogenous gene. The regulatory sequence may be a sequence that encodes a motif which may affect the gene expression. The motif may be, for example, a secondary structure-stabilizing motif, an RNA destabilizing motif, a splice-activating motif, a polyadenylation motif, an adenine-rich sequence, or an endonuclease recognition region.

The increased activity of the protein having a sequence identity of about 95% or more to the at least one of GlnK and GlnD may be obtained by mutation of a gene that encodes the at least one of GlnK and GlnD. The mutation may include substitution, insertion, addition, or conversion of at least one nucleotide of the gene.

The genetically engineered bacteria cell may have a reduced activity of an L-lactate dehydrogenase, a pyruvate oxidase, a phosphotransacetylase, an acetate kinase, an acetate CoA transferase, or a combination thereof.

The genetically engineered bacteria cell may be a cell in which an L-lactate dehydrogenase gene, a pyruvate oxidase gene, a phosphotransacetylase gene, an acetate kinase gene, an acetate CoA transferase gene, or a combination thereof is deleted or disrupted.

The L-lactate dehydrogenase (LDH) may catalyze the conversion of lactate to pyruvate. The LDH may be an enzyme in enzyme class (EC) 1.1.1.27. The LDH may have, for example, an amino acid sequence of SEQ ID NO: 5. An L-lactate dehydrogenase (LDH) gene may encode an amino acid sequence of SEQ ID NO: 5.

The pyruvate oxidase (PoxB) may catalyze the conversion of pyruvate to acetate. The PoxB may be an enzyme in EC. 1.2.5.1. The PoxB may have, for example, an amino acid sequence of SEQ ID NO: 6. A PoxB gene may encode an amino acid sequence of SEQ ID NO: 6.

The phosphotransacetylase (PTA) may catalyze the conversion of acetyl-CoA to acetyl phosphate. The PTA may be an enzyme in EC.2.3.1.8. The PTA may have, for example, an amino acid sequence of SEQ ID NO: 7. A PTA gene may encode an amino acid sequence of SEQ ID NO: 7.

The acetate kinase (Ack) may catalyze the conversion of acetyl phosphate to acetate. The Ack may be an enzyme in EC.2.7.2.1. The Ack may have an amino acid sequence of SEQ ID NO: 8. An Ack gene may encode an amino acid sequence of SEQ ID NO: 8.

The acetate CoA transferase (ActA) may catalyze the conversion of acetyl -CoA to acetate. The ActA may be an enzyme in EC.2.8.3.-. The ActA may have an amino acid sequence of SEQ ID NO: 9. An actA gene may encode an amino acid sequence of SEQ ID NO: 9.

The genetically engineered bacteria cell may have increased activity of pyruvate carboxylase (PYC) that catalyzes the conversion of pyruvate to oxaloacetate. The expression "increased activity" has the meaning as described above. For example, the increased activity may occur by introducing a gene that encodes a mutated PYC having an increased specific activity, into a cell. The mutation may include substitution, addition, or deletion of an amino acid sequence of PYC, or a combination thereof. For example, the substitution may be a substitution of a 458$^{th}$ proline in an amino acid sequence of SEQ ID NO: 10 with serine, i.e., a P458S substitution. For example, the cell may have increased activity of PYC by random mutation or genetical engineering. The PYC may have a sequence of SEQ ID NO: 10 or a sequence of SEQ ID NO: 10 in which the 458$^{th}$ proline is substituted with serine. The PYC gene may encode a sequence of SEQ ID NO: 10 (for example, Ncgl0659) or a sequence of SEQ ID NO: 10 in which the 458$^{th}$ proline is substituted with proline.

According to another embodiment of the present disclosure, a composition for use in production of succinic acid includes any of the genetically engineered bacteria cells according to the above-described embodiments and a suitable cell culture medium.

According to another embodiment of the present disclosure, there is provided use of any of the genetically engineered bacteria cells according to the above-described embodiments in production of succinic acid.

According to another embodiment of the present disclosure, a method of producing an organic acid includes: incubating any of the genetically engineered bacteria cells according to the above-described embodiments in a cell culture medium, whereby the genetically engineered bacterial cell produces succinic acid; and recovering succinic acid from a cultured product.

The incubating may be performed in a suitable medium under suitable incubating conditions known in the art. It is obvious to one of ordinary skill in the art to appropriately change a culture medium and incubating conditions depending on a selected microorganism. For example, the incubating may be performed by batch culturing, continuous culturing, fed-batch culturing, or a combination thereof. Examples of the genetically engineered bacteria cell are as listed above.

The culture medium may include various carbon sources, nitrogen sources, and trace elements.

A carbon source may be, for example, carbohydrate such as glucose, sucrose, lactose, fructose, maltose, starch, or cellulose; fats and oils, such as soybean oil, sunflower oil, castor oil, or coconut oil; fatty acid such as palmitic acid, stearic acid, linoleic acid; alcohol such as glycerol or ethanol; organic acid such as acetic acid, and/or a combination thereof. The incubating may be performed using glucose as the carbon source. A nitrogen source may be an organic nitrogen source such as peptone, yeast extract, beef stock, malt extract, corn steep liquor (CSL), or soybean flour, or an inorganic nitrogen source such as urea, ammonium sulfate, ammonium chloride, ammonium phosphate, ammonium carbonate, and ammonium nitrate, or a combination thereof. The culture medium as a phosphorus supply source may include, for example, potassium dihydrogen phosphate, dipotassium phosphate, and corresponding sodium-containing salt thereof, and a metal salt such as magnesium sulfate or iron sulfate. The culture medium may also include amino acids, vitamins, suitable precursors, or the like. The culture medium or individual components may be added to a culture medium in a fed-batch, or continuous manner.

The pH of the culture medium may be adjusted by adding a compound such as ammonium hydroxide, potassium hydroxide, ammonia, phosphoric acid, and/or sulfuric acid to the culture medium during the incubating process in an appropriate manner. Also, an antifoaming agent such as fatty acid polyglycol ester may be used during the incubating process to inhibit generation of bubbles.

The incubating process may be performed in an aerobic, microaerobic, or anaerobic condition. The term "microaerobic condition" as used herein refers to a condition in which a low level of oxygen that is less than that of the atmospheric oxygen is dissolved in the culture medium. The low level of oxygen may be, for example, about 0.1% to about 10%, about 1% to about 9%, about 2% to about 8%, about 3% to about 7%, or about 4% to about 6% of the dissolved oxygen concentration obtained by limiting the culture medium to contact with atmospheric air. The incubating temperature may be, for example, about 20° C. to about 45° C., or about 25° C. to about 40° C. The incubation period may be maintained until a target quantity of succinic acid is obtained.

The organic acid is as described above. The organic acid, for example, succinic acid, may be recovered by separation and purification methods known in the art. For example, the recovering may be performed by centrifugation, ion exchange chromatography, filtration, precipitation, or a combination thereof. For example, the recovering may be performed by centrifugation of a cultured product to remove biomass and then by ion exchange chromatography of a resulting supernatant.

As described above, according to the one or more embodiments of the present disclosure, the genetically engineered bacteria cell may have an enhanced ability to produce organic acid, and thus may be effectively used to produce organic acid.

Any of the methods of producing organic acid, according to the above-described embodiments of the present disclosure, may effectively produce an organic acid, for example, succinic acid.

One or more embodiments of the present disclosure will now be described in detail with reference to the following examples. However, these examples are only for illustrative purposes and are not intended to limit the scope of the one or more embodiments of the present disclosure.

EXAMPLES

Materials and methods used in the following examples are as follows, unless stated otherwise.

1. Construction of *Corynebacterium* (Δldh), S003, and S006 Strains

*Corynebacterium* S003 strain as a recombinant strain in which the pathway to synthesize lactate and acetate was deleted was constructed using a *Corynebacterium glutamicum* (*C. glutamicum*, CGL) ATCC 13032 as a parent strain.

(1) Construction of Replacement Vector

The genes of L-lactate dehydrogenase (ldh), pyruvate oxidase (poxB), phosphotransacetylase (pta), acetate kinase (ackA), and acetate CoA transferase (actA) gene in *Corynebacterium glutamicum* ATCC 13032 were inactivated by homogeneous recombination using a pK19 mobsacB (ATCC 87098) vector. Two homogeneous sequences for use in the recombination were obtained by amplification via polymerase chain reaction (PCR) using a genomic DNA of the CGL ATCC 13032 as a template.

Two homogeneous sequences for deletion of the ldh gene were upstream and downstream regions of the gene that were obtained by amplification via PCR using a primer set of ldhA_5'_HindIII (SEQ ID NO: 11) and ldhA_up_3'_XhoI (SEQ ID NO: 12) and a primer set of ldhA_dn_5'_XhoI (SEQ ID NO: 13) and ldhA_3'_EcoRI (SEQ ID NO: 14). The PCR amplification was conducted by repeating 30 times of a cycle including denaturation at 95° C. for 30 seconds, annealing at 55° C. for 30 seconds, and extension at 72° C. for 30 seconds. PCR amplification in the following examples was conducted under the same conditions as described above. A resulting amplified product was cloned at the sites of restriction enzymes HindIII and EcoRI of the pK19 mobsacB vector, thereby constructing a pK19_Δldh vector.

Two homogeneous sequences for deletion of the poxB gene were upstream and downstream regions of the gene that were obtained by amplification via PCR using a primer set of poxB 5'_H3 (SEQ ID NO: 15) and DpoxB_up 3' (SEQ ID NO: 16) and a primer set of DpoxB_dn 5' (SEQ ID NO: 17) and poxB 3' E1 (SEQ ID NO: 18). A resulting amplified product was cloned at the sites of restriction enzymes HindIII and EcoRI of the pK19 mobsacB vector, thereby constructing a pK19_ΔpoxB vector.

Two homogeneous sequences for deletion of the pta-ackA gene were upstream and downstream regions of the gene that were obtained by amplification via PCR using a primer set of pta 5' H3 (SEQ ID NO: 19) and Dpta_up_R1 3' (SEQ ID NO: 20) and a primer set of DackA_dn_R1 5' (SEQ ID NO: 21) and ackA 3' Xb (SEQ ID NO: 22). A resulting amplified product was cloned at the sites of restriction enzymes HindIII and EcoRI of the pK19 mobsacB vector, thereby constructing a pK19_Δpta_ackA vector.

Two homogeneous sequences for deletion of the actA gene were upstream and downstream regions of the gene that were obtained by amplification via PCR using a primer set of actA 5' Xb (SEQ ID NO: 23) and DactA_up_R4 3' (SEQ ID NO: 24) and a primer set of DactA_dn_R4 5' (SEQ ID NO: 25) and actA 3' H3 (SEQ ID NO: 26). A resulting amplified product was cloned at the sites of restriction enzymes XbaI and HindIII of the pK19 mobsacB vector, thereby constructing a pK19_ΔactA vector.

To construct a pyruvate carboxylase recombinant ('PYC$^{P458S}$') in which a 458$^{th}$ proline of pyruvate carboxylase (SEQ ID NO: 10) of *C. glutamicum* ATCC 13032 was substituted with serine, the codon CCG encoding the 458$^{th}$ proline of the amino acid sequence of the pyruvate carboxylase (PYC) was replaced with TCG by overlap extension PCR, which was conducted using a genomic DNA of *C. glutamicum* ATCC 13032 as a template and a primer set of pyc-F1 (SEQ ID NO: 27) and pyc-R1 (SEQ ID NO: 28) to obtain a PCR product, followed by PCR using a primer set of pyc-F2 (SEQ ID NO: 29) and pyc-R2 (SEQ ID NO: 30) to obtain a PCR product. PCR was further conducted using the PCR products from the previous two PCRs as a template and a primer set of pyc-F1 and pyc-R2 to obtain a final PCR product. This final PCR product was cloned at the site of restriction enzyme XbaI of the pK19mobsacB vector, thereby constructing a pK19mobsacB-pyc* vector.

(2) Construction of CGL (Δldh), CGL (Δldh, ΔpoxB, Δpta-ackA, ΔactA) [Also Referred to as 'S003'], and CGL (Δldh, ΔpoxB, Δpta-ackA, ΔactA, pyc$^{P458S}$)[Also Referred to as 'S006']

The pK19_Δldh vector, pK19_ΔpoxB, pK19_Δpta_ackA, pK19_ΔactA vector, or pK19mobsacB-pyc* vector constructed as described above was introduced into *C. glutamicum* ATCC13032 by electroporation. 25 μg/mL of each of the vector-introduced strains was streaked on a kanamycin-containing a Luria Brain Heart Infusion supplemented with sorbitol (LBHIS) agar plate and incubated at about 30° C. The LBHIS agar plate contained 25 g/L of Difco LB™ broth, 18.5 g/L of brain-heart infusion broth, 91 g/L of D-sorbitol, and 15 g/L of agar. The composition of the LBHIS medium agar plate was the same in the following examples. The obtained colonies were incubated at 30° C. in a brain heart infusion supplemented (BHIS) medium (pH 7.0) containing 37 g/L of brain heart infusion powder and 91 g/L of D-sorbitol. A resulting culture solution was streaked on a LB/Suc10 agar plate and incubated at about 30° C. to select the colonies in which double-crossing occurred. The used LB/Suc10 agar plate contained 25 g/L of Difco LB™ broth, 15 g/L of agar, and 100 g/L of sucrose.

After separation of a genomic DNA from the selected colonies, whether deletion of the genes occurred or not was identified by PCR, using a primer set of ldhA_5'_HindIII and ldhA_3'_EcoRI to identify the deletion of the ldh gene, a primer set of poxB_up_for (SEQ ID NO: 31) and poxB_dn_rev (SEQ ID NO: 32) to identify the deletion of the poxB gene, a primer set of pta_up_for (SEQ ID NO: 33) and ackA_dn_rev (SEQ ID NO: 34) to identify the deletion of the pta-ackA gene, and a primer set of actA_up_for (SEQ ID NO: 35) and actA_dn_rev (SEQ ID NO: 36) to identify the deletion of the actA gene. To identify the mutation of the pyc gene, PCR was conducted using a primer set of pyc-F1 and pyc-R2, and a resulting PCR product was subjected to sequence analysis to identify whether substitution of the pyc gene occurred or not.

As a result, the CGL recombinant variants, i.e., CGL (Δldh), CGL (Δldh, ΔpoxB, Δpta-ackA, ΔactA) (also referred to as "S003"), and CGL (Δldh, ΔpoxB, Δpta-ackA, ΔactA, pyc$^{P458S}$) (also referred to as "S006") were obtained.

2. Construction of GlnD and GlnK Overexpression Vector

The GlnDK gene or glnD gene was introduced at the site of restriction enzyme HindIII/EcoRI of the pGS-EX4 vector to construct a vector operably linked to a Ptuff promoter.

(1) Construction of pGS-EX Vector

A promoter (Ptuf) of tuf gene (NCgl0480) was cloned at the site of KpnI of pGT1 (SEQ ID NO: 42) that is used as a shuttle vector in *Corynebacterium* and *Escherichia coli* to obtain a pGS-EX4 vector. The Ptuf promoter fragment was amplified using a genomic DNA of *C. glutamicum* ATCC 13032 as a template and a primer set of Tuf-F (SEQ ID NO: 37) and Tuf-R (SEQ ID NO: 38) and then cloned at pGT1 by using a In-Fusion® HD Cloning Kit (Clontech 639648).

(2) Construction of pGS-EX4-glnDK Vector

The glnDK gene of *Corynebacterium glutamicum* ATCC 13032 was amplified by PCR using a primer set of SEQ ID NO: 39 and SEQ ID NO: 40 and a genome of *Corynebacterium glutamicum* 13032 as a template. To express the glnDK gene under a tuf promoter of *Corynebacterium glutamicum*, a resulting PCR product was cloned at the sites of the restriction enzymes of HindIII and EcoRI of the pGS-EX4 vector to obtain a pGS-EX4-glnDK vector as illustrated in FIG. 1.

(3) Construction of pGS-EX4-glnD Vector

Figure 2:
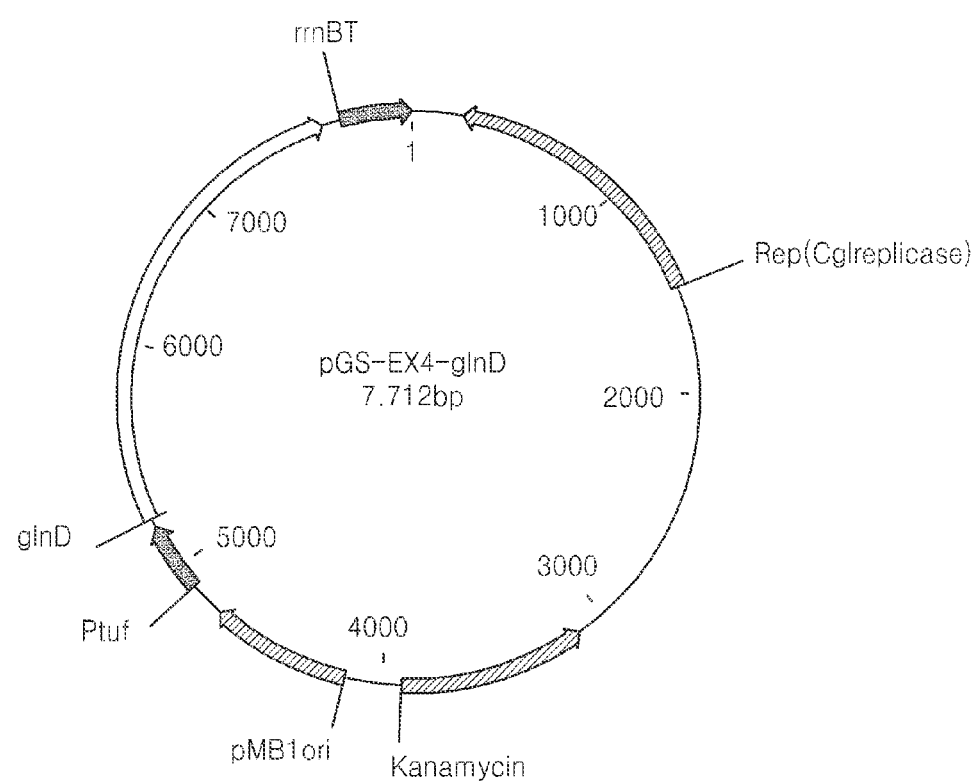
FIG. 2 is a cleavage map of a pGS-EX4-glnD vector.

The glnD gene of *Corynebacterium glutamicum* ATCC 13032 was amplified by PCR using a primer set of SEQ ID NO: 41 and SEQ ID NO: 40 and a genome of *Corynebacterium glutamicum* 13032 as a template. To express the glnD gene under a tuf promoter of *Corynebacterium glutamicum*, a resulting PCR product was cloned at the sites of the restriction enzymes of HindIII and EcoRI of the pGS-EX4 vector to obtain a pGS-EX4-glnD vector as illustrated in FIG. 2.

Example 1

Characterization of glnDK Overexpression or GlnD Overexpression *Corynebacterium glutamicum* Strains

*Corynebacterium glutamicum* strains that overexpress glnDK or glnD were obtained, and then incubated to calculate glucose consumption rates and amounts of produced succinic acid and thus identify incubation characteristics of the strains.

The pGS-EX4-glnDK vector or pGS-EX4-glnD vector were transformed into *Corynebacterium glutamicum* S006 strains by electroporation (1.25 kV/cm, 5 ms) to obtain *Corynebacterium glutamicum* S006 (+glnDK) and S006 (+glnD) strains that overexpress glnDK or glnD A pGS-EX4 vector as an empty vector was transformed into a *Corynebacterium glutamicum* S006 strain to obtain a *Corynebacterium glutamicum* S006 (pGS-EX4) strain as a control group.

For seed culture of the strains, each of the strains was streaked on a LB plate medium (containing 5 g/L of yeast extract, 10 g/L of NaCl, 10 g/L of tryptone, and 15 g/L of agar plate) and incubated at about 30° C. for about 48 hours. A single colony of each of the incubation products was inoculated into 5 mL of a BHIS medium (containing 37 g/L of brain-heart infusion broth and 91 g/L of D-sorbitol, pH 7.0) and then incubated at about 30° C. for about 16 hours.

About 0.5 mL of a resulting culture solution was inoculated into 20 mL of a BHIS medium in a 250 mL of flask, and then incubated until an $OD_{600}$ value reached 6.0, followed by centrifugation of a resulting culture solution. A resulting supernatant was removed to selectively collect microorganisms, which were then washed with a CGXII minimal medium. The used CGXII medium contained 20 g/L of $(NH_4)_2SO_4$, 5 g/L of urea, 1 g/L of $KH_2PO_4$, 1 g/L of $K_2HPO_4$, 0.25 g/L of $MgSO_4.7H_2O$, 10 mg/L of $CaCl_2$, 10 mg/L of $FeSO_4.7H_2O$, 0.1 mg/L of $MnSO_4.H_2O$, 1 mg/L of $ZnSO_4.7H_2O$, 0.2 mg/L of $CuSO_4.5H_2O$, 20 mg/L of $NiCl_2.6H_2O$, 0.2 mg/L of biotin, 42 g/L of (3-(N-morpholino)propanesulfonic acid (MOPS), and 4% (w/v) of glucose. 1 mL of each of the cell cultures suspended in the CGXII medium to reach a $OD_{600}$ value of 30 was put into an 1.5 mL Eppendorf tube, capped, and then incubated at about 30° C. for about 24 hours, followed by centrifugation of a resulting culture solution to collect a supernatant including succinic acid and glucose. The concentrations of succinic acid and glucose in the supernatant were quantized using high-performance liquid chromatography (HPLC).

The results of calculating the glucose consumption rates and the amounts of produced succinic acid in *Corynebacterium glutamicum* S006 (+glnDK) and S006 (+glnD) strains are shown in Table 1.

TABLE 1

| Strain | Production of succinic acid | | Strain | Glucose consumption | |
|---|---|---|---|---|---|
| | Amount (g/l) | Increase rate (%) | | Amount (g/l) | Increase rate (%) |
| S006 (+con) | 3.89 | 0 | S006(+con) | 11.77 | 0 |
| S006 (+glnDK) | 5.78 | 48.59 | S006(+glnDK) | 15.22 | 29.31 |
| S006 (+glnD) | 5.19 | 33.41 | S006(+glnD) | 14.42 | 22.51 |

In Table 1, S006 (+con) denotes a *Corynebacterium glutamicum* S006 strain as a control group into which an empty vector was introduced.

Referring to Table 1, in *Corynebacterium glutamicum* S006 (+glnDK) and S006 (+glnD) strains that overexpress glnDK or glnD, the production of succinic acid and the glucose consumption rates were markedly increased, compared to the control group.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A genetically engineered bacteria cell having an enhanced ability to produce an organic acid, wherein the genetically engineered bacteria cell comprises a genetic modification that increases the activity of GlnK; GlnD or combination thereof, as compared to a parent cell, and wherein the genetically engineered bacteria cell exhibits increased organic acid production compared to a parent cell; wherein the genetic modification that increases the activity of GlnK, GlnD, or a combination thereof comprises an increase in the copy number of a nucleic acid encoding GlnK, GlnD, or combination thereof, or a modification of an expression regulatory sequence of a nucleic acid encoding GlnK, GlnD, or combination thereof;

wherein the organic acid is succinic acid; and wherein the genetically engineered bacteria cell comprises deletion or disruption of an L-lactate dehydrogenase gene, a pyruvate oxidase gene, a phosphotransacetylase gene, an acetate kinase gene, an acetate CoA transferase gene, or a combination thereof.

2. The genetically engineered bacteria cell of claim 1, wherein GlnK and GlnD are encoded by SEQ ID NO: 3 and SEQ ID NO: 4, respectively.

3. The genetically engineered bacteria cell of claim 1, wherein the genetically engineered bacteria cell produces succinic acid under microaerobic or anaerobic conditions.

4. The genetically engineered bacteria cell of claim 1, wherein the genetically engineered bacteria cell is a *Corynebacterium* cell.

5. The genetically engineered bacteria cell of claim 1, wherein the genetically engineered bacteria cell comprises an exogenous nucleic acid encoding GlnK, GlnD or combination thereof.

6. The genetically engineered bacteria cell of claim 1, wherein the genetically engineered bacteria cell comprises an amplified endogenous gene encoding GlnK, GlnD or combination thereof.

7. The genetically engineered bacteria cell of claim 1, wherein the genetically engineered bacteria cell comprises increased pyruvate carboxylase activity in the conversion of pyruvate to oxaloacetate compared to a parent cell.

8. The genetically engineered bacteria cell of claim 7, wherein the pyruvate carboxylase comprises SEQ ID NO: 10 with a P458S substitution.

9. A method of producing succinic acid, the method comprising:

incubating the genetically engineered bacteria cell of claim 1 in a cell culture medium, whereby the genetically engineered bacterial cell produces succinic acid; and recovering succinic acid from the culture.

10. The method of claim 9, wherein the incubating is performed under microaerobic or anaerobic conditions.

11. The method of claim 9, wherein the genetically engineered bacteria cell is a *Corynebacterium* cell.

12. The method of claim 9, wherein the genetically engineered bacterial cell comprises increased pyruvate carboxylase activity in conversion of pyruvate to oxaloacetate compared to a parent cell.

13. A method of producing a genetically engineered bacteria cell with increased organic acid production according to claim 1, the method comprising introducing a genetic modification that increases the activity of GlnK, GlnD, or combination thereof in a bacteria cell; and deleting or disrupting an L-lactate dehydrogenase gene, a pyruvate oxidase gene, a phosphotransacetylase gene, an acetate kinase gene, an acetate CoA transferase gene, or a combination thereof in the bacterial cell;

wherein the genetic modification that increases the activity of GlnK, GlnD, or a combination thereof comprises an increase in the copy number of a nucleic acid encoding GlnK, GlnD, or combination thereof, or a modification of an expression regulatory sequence of a nucleic acid encoding GlnK, GlnD, or combination thereof; and wherein the bacterial cell has increased organic acid production of succinic acid.

* * * * *

SEQUENCE LISTING

```
<160> NUMBER OF SEQ ID NOS: 42

<210> SEQ ID NO 1
<211> LENGTH: 112
<212> TYPE: PRT
<213> ORGANISM: Corynebacterium Glutamicum
<220> FEATURE:
<221> NAME/KEY: MISC FEATURE
<222> LOCATION: (1)..(112)
<223> OTHER INFORMATION: ATCC13032

<400> SEQUENCE: 1

Met Lys Leu Ile Thr Ala Ile Val Lys Pro Phe Thr Leu Thr Asp Ile
 1               5                  10                  15

Lys Asp Ala Leu Glu Gln Ala Gly Val Gln Gly Met Thr Val Thr Glu
             20                  25                  30

Thr Gln Gly Phe Gly Gln Gln Lys Gly His Thr Glu Val Tyr Arg Gly
         35                  40                  45

Ala Glu Tyr Ala Val Asp Phe Val Pro Lys Val Lys Ile Glu Val Ile
     50                  55                  60

Ile Ser Asp Ala Gln Ala Glu Glu Val Ile Asn Ile Ile Val Glu Thr
 65                  70                  75                  80

Ala Arg Thr Gly Lys Val Gly Asp Gly Lys Val Trp Met Thr Asn Ile
                 85                  90                  95

Glu Glu Leu Val Arg Val Arg Thr Gly Glu Arg Gly Glu Ala Ala Leu
            100                 105                 110

<210> SEQ ID NO 2
<211> LENGTH: 692
<212> TYPE: PRT
<213> ORGANISM: Corynebacterium Glutamicum
<220> FEATURE:
<221> NAME/KEY: MISC FEATURE
<222> LOCATION: (1)..(692)
<223> OTHER INFORMATION: ATCC13032

<400> SEQUENCE: 2

Met Asn Asn Pro Ala Gln Leu Arg Gln Asp Thr Glu Lys Glu Val Leu
 1               5                  10                  15

Ala Leu Leu Gly Ser Leu Val Leu Pro Ala Gly Thr Ala Leu Ala Ala
             20                  25                  30

Thr Gly Ser Leu Ala Arg Ser Glu Leu Thr Pro Tyr Ser Asp Leu Asp
         35                  40                  45

Leu Ile Leu Ile His Pro Pro Gly Ala Thr Pro Asp Gly Val Glu Asp
     50                  55                  60

Leu Trp Tyr Pro Ile Trp Asp Ala Lys Lys Arg Leu Asp Tyr Ser Val
 65                  70                  75                  80

Arg Thr Pro Asp Glu Cys Val Ala Met Ile Ser Ala Asp Ser Thr Ala
                 85                  90                  95

Ala Leu Ala Met Leu Asp Leu Arg Phe Val Ala Gly Asp Glu Asp Leu
            100                 105                 110

Cys Ala Lys Thr Arg Arg Arg Ile Val Glu Lys Trp Arg Gln Glu Leu
            115                 120                 125
```

```
Asn Lys Asn Phe Asp Ala Val Val Asp Thr Ala Ile Ala Arg Trp Arg
    130                 135                 140
Arg Ser Gly Pro Val Val Ala Met Thr Arg Pro Asp Leu Lys His Gly
145                 150                 155                 160
Arg Gly Gly Leu Arg Asp Phe Glu Leu Ile Lys Ala Leu Ala Leu Gly
                165                 170                 175
His Leu Cys Asn Leu Pro Gln Leu Asp Ala Gln His Gln Leu Leu Leu
            180                 185                 190
Asp Ala Arg Thr Leu Leu His Val His Ala Arg Arg Ser Arg Asp Val
        195                 200                 205
Leu Asp Pro Glu Phe Ala Val Asp Val Ala Met Asp Leu Gly Phe Val
    210                 215                 220
Asp Arg Tyr His Leu Gly Arg Glu Ile Ala Asp Ala Ala Arg Ala Ile
225                 230                 235                 240
Asp Asp Gly Leu Thr Thr Ala Leu Ala Thr Ala Arg Gly Ile Leu Pro
                245                 250                 255
Arg Arg Thr Gly Phe Ala Phe Arg Asn Ala Ser Arg Arg Pro Leu Asp
            260                 265                 270
Leu Asp Val Val Asp Ala Asn Gly Thr Ile Glu Leu Ser Lys Lys Pro
        275                 280                 285
Asp Leu Asn Asp Pro Ala Leu Pro Leu Arg Val Ala Ala Ala Ala
    290                 295                 300
Thr Thr Gly Leu Pro Val Ala Glu Ser Thr Trp Val Arg Leu Asn Glu
305                 310                 315                 320
Cys Pro Pro Leu Pro Glu Pro Trp Pro Ala Asn Ala Ala Gly Asp Phe
                325                 330                 335
Phe Arg Ile Leu Ser Ser Pro Lys Asn Ser Arg Arg Val Val Lys Asn
            340                 345                 350
Met Asp Arg His Gly Leu Trp Ser Arg Phe Val Pro Glu Trp Asp Arg
        355                 360                 365
Ile Lys Gly Leu Met Pro Arg Glu Pro Ser His Ile Ser Thr Ile Asp
    370                 375                 380
Glu His Ser Leu Asn Thr Val Ala Gly Cys Ala Leu Glu Thr Val Thr
385                 390                 395                 400
Val Ala Arg Pro Asp Leu Leu Val Leu Gly Ala Leu Tyr His Asp Ile
                405                 410                 415
Gly Lys Gly Phe Pro Arg Pro His Glu Gln Val Gly Ala Glu Met Val
            420                 425                 430
Ala Arg Ala Ala Ser Arg Met Gly Leu Asn Leu Arg Asp Arg Ala Ser
        435                 440                 445
Val Gln Thr Leu Val Ala Glu His Thr Ala Val Ala Lys Ile Ala Ala
    450                 455                 460
Arg Leu Asp Pro Ser Ser Glu Gly Ala Val Asp Lys Leu Leu Asp Ala
465                 470                 475                 480
Val Arg Tyr Asp Leu Val Thr Leu Asn Leu Leu Glu Val Leu Thr Glu
                485                 490                 495
Ala Asp Ala Lys Ala Thr Gly Pro Gly Val Trp Thr Ala Arg Leu Glu
            500                 505                 510
His Ala Leu Arg Ile Val Cys Lys Arg Ala Arg Asp Arg Leu Thr Asp
        515                 520                 525
Ile Arg Pro Val Ala Pro Met Ile Ala Pro Arg Ser Glu Ile Gly Leu
    530                 535                 540
Val Glu Arg Asp Gly Val Phe Thr Val Gln Trp His Gly Glu Asp Leu
```

```
                545                 550                 555                 560
His Arg Ile Leu Gly Val Ile Tyr Ala Lys Gly Trp Thr Ile Thr Ala
                        565                 570                 575

Ala Arg Met Leu Ala Asn Gly Gln Trp Ser Ala Glu Phe Asp Val Arg
                580                 585                 590

Ala Asn Gly Pro Gln Asp Phe Asp Pro Gln His Phe Leu Gln Ala Tyr
                595                 600                 605

Gln Ser Gly Val Phe Ser Glu Val Pro Ile Pro Ala Leu Gly Ile Thr
        610                 615                 620

Ala Thr Phe Trp His Gly Asn Thr Leu Glu Val Arg Thr Glu Leu Arg
625                 630                 635                 640

Thr Gly Ala Ile Phe Ala Leu Leu Arg Thr Leu Pro Asp Ala Leu Trp
                        645                 650                 655

Ile Asn Ala Val Thr Arg Gly Ala Thr Leu Ile Ile Gln Ala Ala Leu
                660                 665                 670

Lys Pro Gly Phe Asp Arg Ala Thr Val Glu Arg Ser Val Val Arg Ser
                675                 680                 685

Leu Ala Gly Ser
        690

<210> SEQ ID NO 3
<211> LENGTH: 339
<212> TYPE: DNA
<213> ORGANISM: Corynebacterium Glutamicum
<220> FEATURE:
<221> NAME/KEY: MISC FEATURE
<222> LOCATION: (1)..(339)
<223> OTHER INFORMATION: ATCC13032

<400> SEQUENCE: 3
atgaaactca tcaccgcaat tgtcaagccg tttaccctca ccgacattaa agatgctctc      60
gagcaggcag gtgtgcaggg catgactgtc accgaaaccc aaggctttgg ccagcagaaa     120
ggccacaccg aggtgtaccg tggtgctgaa tacgctgtcg attttgtgcc taaggtcaag     180
attgaagtta ttatctccga tgctcaggct gaggaagtca tcaacattat cgtcgagacc     240
gcacgcaccg gcaaagtcgg cgacggcaaa gtgtggatga ctaacatcga agagctggtt     300
cgtgttcgta ccggtgagcg cggcgaagca gccctttaa                           339

<210> SEQ ID NO 4
<211> LENGTH: 2079
<212> TYPE: DNA
<213> ORGANISM: Corynebacterium Glutamicum
<220> FEATURE:
<221> NAME/KEY: MISC FEATURE
<222> LOCATION: (1)..(2079)
<223> OTHER INFORMATION: ATCC13032

<400> SEQUENCE: 4
atgaataatc cagcccagct gcgccaagat actgaaaagg aagtcctggc gttgctgggc      60
tctttggttt acccgccggg caccgcgctt gccgccaccg atctttggc caggtccgaa     120 ctcacgccgt attccgattt ggacctcatt ttgatccatc caccaggagc acccccggat     180
ggcgtggagg atttgtggta cccgatttgg gacgcaaaaa agcgtctcga ctactccgtg     240 cgcacccag atgagtgtgt ggctatgatt tctgcggatt ccactgcagc ccttgccatg     300
cttgacctgc ggtttgtcgc tggcgatgag gatctgtgtg ccaaaacgcg ccggcgcatc     360
gtggagaagt ggcgccagga actcaacaaa aacttcgatg ccgttgtgga caccgcgatt     420
```

| | |
|---|---|
| gcccgttggc gccgctccgg acccgtcgtg gcaatgacgc ggccagatct taaacacggc | 480 |
| aggggagggc tgcgcgattt cgaactgatc aaggccctcg cgctcggcca cctatgcaac | 540 |
| cttccacagc ttgatgcgca acaccagctg cttctcgacg cccgcacctt gctgcacgtc | 600 |
| cacgcgcgac gctcccgcga cgtccttgac cccgaatttg cggtggatgt ggccatggat | 660 |
| ttgggctttg ttgaccgcta tcacctgggc cgggagatcg ccgatgcagc ccgcgccatt | 720 |
| gatgatggcc tgaccaccgc gctggccacc gcccgtggca ttttgccacg tcgcacaggt | 780 |
| tttgcattca ggaatgcttc tcgacgccca cttgatcttg atgtcgtcga cgccaacggc | 840 |
| accatcgaat tgtccaaaaa accagatctt aatgatcccg cacttccact tcgagtggcc | 900 |
| gcagccgcag caaccaccgg acttccggtg cagaatcaa cctgggttcg acttaatgaa | 960 |
| tgcccgccac ttcctgagcc atggcctgcc aatgcagcag gggacttctt tcggattctc | 1020 |
| tccagtccga aaactcacg ccgagtggtg aaaaatatgg atcgccacgg attgtggtcg | 1080 |
| cgttttgttc cagaatggga ccgcatcaaa gggcttatgc cccgtgaacc cagccatatt | 1140 |
| tccaccatcg atgaacatag tctgaacact gttgcaggat gtgcgctaga aactgtgacc | 1200 |
| gtcgcgcgcc ccgatctttt agttttggga gccttgtacc acgacattgg caagggcttc | 1260 |
| ccgcgtccac acgaacaagt aggtgcagag atggtggcga gggctgcaag ccgcatggga | 1320 |
| ttgaaccttc gcgatcgtgc cagcgtgcaa acgctggtcg ccgagcacac cgcggtggcc | 1380 |
| aaaatcgccg cgcgccttga tccctcctcg gagggcgccg tcgataagct gcttgatgct | 1440 |
| gttaggtatg acctggtgac attgaatctg cttgaggtgc taacagaagc tgatgcgaaa | 1500 |
| gccacggggc ctggcgtgtg gacggcgcgt tggagcatg cgctgcggat tgtgtgcaag | 1560 |
| cgtgcgcgtg atcgcctcac cgatattcgc ccggttgcgc cgatgattgc gccacgtagt | 1620 |
| gaaattggtt tggtggaacg cgatggcgtg ttcacagtgc aatggcacgg cgaagactta | 1680 |
| catcggattc ttggcgtaat ttatgccaaa ggatggacaa tcaccgcggc gcgcatgctg | 1740 |
| gccaatggtc aatggagtgc ggaatttgat gtccgcgcaa acggccccca agattttgat | 1800 |
| ccgcagcatt tcctgcaggc atatcaatcc ggtgtgtttt ccgaggttcc cattccagca | 1860 |
| cttgggataa cagccacatt ttggcacggg aacactttag aagtgcgcac tgagcttcgc | 1920 |
| acaggagcta ttttgcccct gctcagaaca ttgcccgatg ccctctggat caacgctgtg | 1980 |
| acccgcggtg cgaccctgat tatccaggca gcactgaagc ccggcttcga tcgagcaacg | 2040 |
| gtggaacgct ccgtagtcag gtcgttggca ggtagctga | 2079 |

<210> SEQ ID NO 5
<211> LENGTH: 314
<212> TYPE: PRT
<213> ORGANISM: Corynebacterium glutamicum
<220> FEATURE:
<221> NAME/KEY: MISC_FEATURE
<222> LOCATION: (1)..(314)
<223> OTHER INFORMATION: ATCC13032

<400> SEQUENCE: 5

Met Lys Glu Thr Val Gly Asn Lys Ile Val Leu Ile Gly Ala Gly Asp
1               5                   10                  15

Val Gly Val Ala Tyr Ala Tyr Ala Leu Ile Asn Gln Gly Met Ala Asp
            20                  25                  30

His Leu Ala Ile Ile Asp Ile Asp Glu Lys Lys Leu Glu Gly Asn Val
        35                  40                  45

Met Asp Leu Asn His Gly Val Val Trp Ala Asp Ser Arg Thr Arg Val
    50                  55                  60

```
Thr Lys Gly Thr Tyr Ala Asp Cys Glu Asp Ala Ala Met Val Val Ile
 65                  70                  75                  80

Cys Ala Gly Ala Ala Gln Lys Pro Gly Glu Thr Arg Leu Gln Leu Val
                 85                  90                  95

Asp Lys Asn Val Lys Ile Met Lys Ser Ile Val Gly Asp Val Met Asp
            100                 105                 110

Ser Gly Phe Asp Gly Ile Phe Leu Val Ala Ser Asn Pro Val Asp Ile
        115                 120                 125

Leu Thr Tyr Ala Val Trp Lys Phe Ser Gly Leu Glu Trp Asn Arg Val
    130                 135                 140

Ile Gly Ser Gly Thr Val Leu Asp Ser Ala Arg Phe Arg Tyr Met Leu
145                 150                 155                 160

Gly Glu Leu Tyr Glu Val Ala Pro Ser Ser Val His Ala Tyr Ile Ile
                165                 170                 175

Gly Glu His Gly Asp Thr Glu Leu Pro Val Leu Ser Ser Ala Thr Ile
            180                 185                 190

Ala Gly Val Ser Leu Ser Arg Met Leu Asp Lys Asp Pro Glu Leu Glu
        195                 200                 205

Gly Arg Leu Glu Lys Ile Phe Glu Asp Thr Arg Asp Ala Ala Tyr His
    210                 215                 220

Ile Ile Asp Ala Lys Gly Ser Thr Ser Tyr Gly Ile Gly Met Gly Leu
225                 230                 235                 240

Ala Arg Ile Thr Arg Ala Ile Leu Gln Asn Gln Asp Val Ala Val Pro
                245                 250                 255

Val Ser Ala Leu Leu His Gly Glu Tyr Gly Glu Glu Asp Ile Tyr Ile
            260                 265                 270

Gly Thr Pro Ala Val Val Asn Arg Arg Gly Ile Arg Arg Val Val Glu
        275                 280                 285

Leu Glu Ile Thr Asp His Glu Met Glu Arg Phe Lys His Ser Ala Asn
    290                 295                 300

Thr Leu Arg Glu Ile Gln Lys Gln Phe Phe
305                 310

<210> SEQ ID NO 6
<211> LENGTH: 579
<212> TYPE: PRT
<213> ORGANISM: Corynebacterium Glutamicum
<220> FEATURE:
<221> NAME/KEY: MISC FEATURE
<222> LOCATION: (1)..(579)
<223> OTHER INFORMATION: ATCC13032

<400> SEQUENCE: 6

Met Ala His Ser Tyr Ala Glu Gln Leu Ile Asp Thr Leu Glu Ala Gln
 1               5                  10                  15

Gly Val Lys Arg Ile Tyr Gly Leu Val Gly Asp Ser Leu Asn Pro Ile
                20                  25                  30

Val Asp Ala Val Arg Gln Ser Asp Ile Glu Trp Val His Val Arg Asn
            35                  40                  45

Glu Glu Ala Ala Ala Phe Ala Ala Gly Ala Glu Ser Leu Ile Thr Gly
        50                  55                  60

Glu Leu Ala Val Cys Ala Ala Ser Cys Gly Pro Gly Asn Thr His Leu
 65                  70                  75                  80

Ile Gln Gly Leu Tyr Asp Ser His Arg Asn Gly Ala Lys Val Leu Ala
                85                  90                  95
```

-continued

```
Ile Ala Ser His Ile Pro Ser Ala Gln Ile Gly Ser Thr Phe Phe Gln
                100                 105                 110

Glu Thr His Pro Glu Ile Leu Phe Lys Glu Cys Ser Gly Tyr Cys Glu
            115                 120                 125

Met Val Asn Gly Gly Gln Gly Glu Arg Ile Leu His His Ala Ile
        130                 135                 140

Gln Ser Thr Met Ala Gly Lys Gly Val Ser Val Val Ile Pro Gly
145                 150                 155                 160

Asp Ile Ala Lys Glu Asp Ala Gly Asp Gly Thr Tyr Ser Asn Ser Thr
                165                 170                 175

Ile Ser Ser Gly Thr Pro Val Val Phe Pro Asp Pro Thr Glu Ala Ala
                180                 185                 190

Ala Leu Val Glu Ala Ile Asn Asn Ala Lys Ser Val Thr Leu Phe Cys
            195                 200                 205

Gly Ala Gly Val Lys Asn Ala Arg Ala Gln Val Leu Glu Leu Ala Glu
        210                 215                 220

Lys Ile Lys Ser Pro Ile Gly His Ala Leu Gly Gly Lys Gln Tyr Ile
225                 230                 235                 240

Gln His Glu Asn Pro Phe Glu Val Gly Met Ser Gly Leu Leu Gly Tyr
                245                 250                 255

Gly Ala Cys Val Asp Ala Ser Asn Glu Ala Asp Leu Leu Ile Leu Leu
            260                 265                 270

Gly Thr Asp Phe Pro Tyr Ser Asp Phe Leu Pro Lys Asp Asn Val Ala
        275                 280                 285

Gln Val Asp Ile Asn Gly Ala His Ile Gly Arg Arg Thr Thr Val Lys
        290                 295                 300

Tyr Pro Val Thr Gly Asp Val Ala Ala Thr Ile Glu Asn Ile Leu Pro
305                 310                 315                 320

His Val Lys Glu Lys Thr Asp Arg Ser Phe Leu Asp Arg Met Leu Lys
                325                 330                 335

Ala His Glu Arg Lys Leu Ser Ser Val Val Glu Thr Tyr Thr His Asn
            340                 345                 350

Val Glu Lys His Val Pro Ile His Pro Glu Tyr Val Ala Ser Ile Leu
        355                 360                 365

Asn Glu Leu Ala Asp Lys Asp Ala Val Phe Thr Val Asp Thr Gly Met
        370                 375                 380

Cys Asn Val Trp His Ala Arg Tyr Ile Glu Asn Pro Glu Gly Thr Arg
385                 390                 395                 400

Asp Phe Val Gly Ser Phe Arg His Gly Thr Met Ala Asn Ala Leu Pro
                405                 410                 415

His Ala Ile Gly Ala Gln Ser Val Asp Arg Asn Arg Gln Val Ile Ala
            420                 425                 430

Met Cys Gly Asp Gly Gly Leu Gly Met Leu Leu Gly Glu Leu Leu Thr
        435                 440                 445

Val Lys Leu His Gln Leu Pro Leu Lys Ala Val Phe Asn Asn Ser
450                 455                 460

Ser Leu Gly Met Val Lys Leu Glu Met Leu Val Glu Gly Gln Pro Glu
465                 470                 475                 480

Phe Gly Thr Asp His Glu Glu Val Asn Phe Ala Glu Ile Ala Ala Ala
                485                 490                 495

Ala Gly Ile Lys Ser Val Arg Ile Thr Asp Pro Lys Lys Val Arg Glu
            500                 505                 510

Gln Leu Ala Glu Ala Leu Ala Tyr Pro Gly Pro Val Leu Ile Asp Ile
```

-continued

```
                515                 520                 525
Val Thr Asp Pro Asn Ala Leu Ser Ile Pro Thr Ile Thr Trp Glu
        530                 535                 540

Gln Val Met Gly Phe Ser Lys Ala Ala Thr Arg Thr Val Phe Gly Gly
545                 550                 555                 560

Gly Val Gly Ala Met Ile Asp Leu Ala Arg Ser Asn Ile Arg Asn Ile
                565                 570                 575

Pro Thr Pro

<210> SEQ ID NO 7
<211> LENGTH: 461
<212> TYPE: PRT
<213> ORGANISM: Corynebacterium Glutamicum
<220> FEATURE:
<221> NAME/KEY: MISC FEATURE
<222> LOCATION: (1)..(461)
<223> OTHER INFORMATION: ATCC13032

<400> SEQUENCE: 7

Met Ser Asp Thr Pro Thr Ser Ala Leu Ile Thr Thr Val Asn Arg Ser
 1               5                  10                  15

Phe Asp Gly Phe Asp Leu Glu Glu Val Ala Ala Asp Leu Gly Val Arg
                20                  25                  30

Leu Thr Tyr Leu Pro Asp Glu Glu Leu Glu Val Ser Lys Val Leu Ala
            35                  40                  45

Ala Asp Leu Leu Ala Glu Gly Pro Ala Leu Ile Ile Gly Val Gly Asn
        50                  55                  60

Thr Phe Phe Asp Ala Gln Val Ala Ala Ala Leu Gly Val Pro Val Leu
65                  70                  75                  80

Leu Leu Val Asp Lys Gln Gly Lys His Val Ala Leu Ala Arg Thr Gln
                85                  90                  95

Val Asn Asn Ala Gly Ala Val Ala Ala Ala Phe Thr Ala Glu Gln
                100                 105                 110

Glu Pro Met Pro Asp Lys Leu Arg Lys Ala Val Arg Asn His Ser Asn
            115                 120                 125

Leu Glu Pro Val Met Ser Ala Glu Leu Phe Glu Asn Trp Leu Leu Lys
        130                 135                 140

Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
                165                 170                 175

Asp Ile Thr Ile Leu Gly Asp Pro Val Lys Ile Lys Glu Arg Ala Thr
            180                 185                 190

Glu Leu Gly Leu His Leu Asn Thr Ala Tyr Leu Val Asn Pro Leu Thr
        195                 200                 205

Asp Pro Arg Leu Glu Glu Phe Ala Glu Gln Phe Ala Glu Leu Arg Lys
    210                 215                 220

Ser Lys Ser Val Thr Ile Asp Glu Ala Arg Glu Ile Met Lys Asp Ile
225                 230                 235                 240

Ser Tyr Phe Gly Thr Met Met Val His Asn Gly Asp Ala Asp Gly Met
                245                 250                 255

Val Ser Gly Ala Ala Asn Thr Thr Ala His Thr Ile Lys Pro Ser Phe
            260                 265                 270

Gln Ile Ile Lys Thr Val Pro Glu Ala Ser Val Val Ser Ser Ile Phe
        275                 280                 285
```

```
Leu Met Val Leu Arg Gly Arg Leu Trp Ala Phe Gly Asp Cys Ala Val
    290                 295                 300

Asn Pro Asn Pro Thr Ala Glu Gln Leu Gly Glu Ile Ala Val Val Ser
305                 310                 315                 320

Ala Lys Thr Ala Ala Gln Phe Gly Ile Asp Pro Arg Val Ala Ile Leu
                325                 330                 335

Ser Tyr Ser Thr Gly Asn Ser Gly Gly Ser Asp Val Asp Arg Ala
                340                 345                 350

Ile Asp Ala Leu Ala Glu Ala Arg Arg Leu Asn Pro Glu Leu Cys Val
            355                 360                 365

Asp Gly Pro Leu Gln Phe Asp Ala Ala Val Asp Pro Gly Val Ala Arg
    370                 375                 380

Lys Lys Met Pro Asp Ser Asp Val Ala Gly Gln Ala Asn Val Phe Ile
385                 390                 395                 400

Phe Pro Asp Leu Glu Ala Gly Asn Ile Gly Tyr Lys Thr Ala Gln Arg
                405                 410                 415

Thr Gly His Ala Leu Ala Val Gly Pro Ile Leu Gln Gly Leu Asn Lys
            420                 425                 430

Pro Val Asn Asp Leu Ser Arg Gly Ala Thr Val Pro Asp Ile Val Asn
    435                 440                 445

Thr Val Ala Ile Thr Ala Ile Gln Ala Gly Gly Arg Ser
    450                 455                 460

<210> SEQ ID NO 8
<211> LENGTH: 397
<212> TYPE: PRT
<213> ORGANISM: Corynebacterium Glutamicum
<220> FEATURE:
<221> NAME/KEY: MISC FEATURE
<222> LOCATION: (1)..(397)
<223> OTHER INFORMATION: ATCC13032

<400> SEQUENCE: 8

Met Ala Leu Ala Leu Val Leu Asn Ser Gly Ser Ser Ile Lys Phe
1               5                   10                  15

Gln Leu Val Asn Pro Glu Asn Ser Ala Ile Asp Glu Pro Tyr Val Ser
                20                  25                  30

Gly Leu Val Glu Gln Ile Gly Glu Pro Asn Gly Arg Ile Val Leu Lys
            35                  40                  45

Ile Glu Gly Glu Lys Tyr Thr Leu Glu Thr Pro Ile Ala Asp His Ser
    50                  55                  60

Glu Gly Leu Asn Leu Ala Phe Asp Leu Met Asp Gln His Asn Cys Gly
65                  70                  75                  80

Pro Ser Gln Leu Glu Ile Thr Ala Val Gly His Arg Val Val His Gly
                85                  90                  95

Gly Ile Leu Phe Ser Ala Pro Glu Leu Ile Thr Asp Glu Ile Val Glu
            100                 105                 110

Met Ile Arg Asp Leu Ile Pro Leu Ala Pro Leu His Asn Pro Ala Asn
    115                 120                 125

Val Asp Gly Ile Asp Val Ala Arg Lys Ile Leu Pro Asp Val Pro His
130                 135                 140

Val Ala Val Phe Asp Thr Gly Phe Phe His Ser Leu Pro Pro Ala Ala
145                 150                 155                 160

Ala Leu Tyr Ala Ile Asn Lys Asp Val Ala Ala Glu His Gly Ile Arg
                165                 170                 175

Arg Tyr Gly Phe His Gly Thr Ser His Glu Phe Val Ser Lys Arg Val
```

```
            180                 185                 190
Val Glu Ile Leu Glu Lys Pro Thr Glu Asp Ile Asn Thr Ile Thr Phe
        195                 200                 205

His Leu Gly Asn Gly Ala Ser Met Ala Ala Val Gln Gly Gly Arg Ala
    210                 215                 220

Val Asp Thr Ser Met Gly Met Thr Pro Leu Ala Gly Leu Val Met Gly
225                 230                 235                 240

Thr Arg Ser Gly Asp Ile Asp Pro Gly Ile Val Phe His Leu Ser Arg
                245                 250                 255

Thr Ala Gly Met Ser Ile Asp Glu Ile Asp Asn Leu Leu Asn Lys Lys
            260                 265                 270

Ser Gly Val Lys Gly Leu Ser Gly Val Asn Asp Phe Arg Glu Leu Arg
        275                 280                 285

Glu Met Ile Asp Asn Asn Asp Gln Asp Ala Trp Ser Ala Tyr Asn Ile
    290                 295                 300

Tyr Ile His Gln Leu Arg Arg Tyr Leu Gly Ser Tyr Met Val Ala Leu
305                 310                 315                 320

Gly Arg Val Asp Thr Ile Val Phe Thr Ala Gly Val Gly Glu Asn Ala
                325                 330                 335

Gln Phe Val Arg Glu Asp Ala Leu Ala Gly Leu Glu Met Tyr Gly Ile
            340                 345                 350

Glu Ile Asp Pro Glu Arg Asn Ala Leu Pro Asn Asp Gly Pro Arg Leu
        355                 360                 365

Ile Ser Thr Asp Ala Ser Lys Val Lys Val Phe Val Ile Pro Thr Asn
    370                 375                 380

Glu Glu Leu Ala Ile Ala Arg Tyr Ala Val Lys Phe Ala
385                 390                 395

<210> SEQ ID NO 9
<211> LENGTH: 502
<212> TYPE: PRT
<213> ORGANISM: Corynebacterium Glutamicum
<220> FEATURE:
<221> NAME/KEY: MISC FEATURE
<222> LOCATION: (1)..(502)
<223> OTHER INFORMATION: ATCC13032

<400> SEQUENCE: 9

Met Ser Asp Arg Ile Ala Ser Glu Lys Leu Arg Ser Lys Leu Met Ser
  1               5                  10                  15

Ala Asp Glu Ala Ala Gln Phe Val Asn His Gly Asp Lys Val Gly Phe
                20                  25                  30

Ser Gly Phe Thr Gly Ala Gly Tyr Pro Lys Ala Leu Pro Thr Ala Ile
            35                  40                  45

Ala Asn Arg Ala Lys Glu Ala His Gly Ala Gly Asn Asp Tyr Ala Ile
        50                  55                  60

Asp Leu Phe Thr Gly Ala Ser Thr Ala Pro Asp Cys Asp Gly Val Leu
 65                  70                  75                  80

Ala Glu Ala Asp Ala Ile Arg Trp Arg Met Pro Tyr Ala Ser Asp Pro
                85                  90                  95

Ile Met Arg Asn Lys Ile Asn Ser Gly Ser Met Gly Tyr Ser Asp Ile
            100                 105                 110

His Leu Ser His Ser Gly Gln Gln Val Glu Glu Gly Phe Phe Gly Gln
        115                 120                 125

Leu Asn Val Ala Val Ile Glu Ile Thr Arg Ile Thr Glu Glu Gly Tyr
    130                 135                 140
```

Ile Ile Pro Ser Ser Ser Val Gly Asn Asn Val Glu Trp Leu Asn Ala
145                 150                 155                 160

Ala Glu Lys Val Ile Leu Glu Val Asn Ser Trp Gln Ser Glu Asp Leu
            165                 170                 175

Glu Gly Met His Asp Ile Trp Ser Val Pro Ala Leu Pro Asn Arg Ile
            180                 185                 190

Ala Val Pro Ile Asn Lys Pro Gly Asp Arg Ile Gly Lys Thr Tyr Ile
            195                 200                 205

Glu Phe Asp Thr Asp Lys Val Val Ala Val Val Glu Thr Asn Thr Ala
210                 215                 220

Asp Arg Asn Ala Pro Phe Lys Pro Val Asp Ile Ser Lys Lys Ile
225                 230                 235                 240

Ala Gly Asn Phe Leu Asp Phe Leu Glu Ser Glu Val Ala Ala Gly Arg
            245                 250                 255

Leu Ser Tyr Asp Gly Tyr Ile Met Gln Ser Gly Val Gly Asn Val Pro
            260                 265                 270

Asn Ala Val Met Ala Gly Leu Leu Glu Ser Lys Phe Glu Asn Ile Gln
            275                 280                 285

Ala Tyr Thr Glu Val Ile Gln Asp Gly Met Val Asp Leu Ile Asp Ala
            290                 295                 300

Gly Lys Met Thr Val Ala Ser Ala Thr Ser Phe Ser Leu Ser Pro Glu
305                 310                 315                 320

Tyr Ala Glu Lys Met Asn Asn Glu Ala Lys Arg Tyr Arg Glu Ser Ile
            325                 330                 335

Ile Leu Arg Pro Gln Gln Ile Ser Asn His Pro Glu Val Ile Arg Arg
            340                 345                 350

Val Gly Leu Ile Ala Thr Asn Gly Leu Ile Glu Ala Asp Ile Tyr Gly
            355                 360                 365

Asn Val Asn Ser Thr Asn Val Ser Gly Ser Arg Val Met Asn Gly Ile
            370                 375                 380

Gly Gly Ser Gly Asp Phe Thr Arg Asn Gly Tyr Ile Ser Ser Phe Ile
385                 390                 395                 400

Thr Pro Ser Glu Ala Lys Gly Gly Ala Ile Ser Ala Ile Val Pro Phe
            405                 410                 415

Ala Ser His Ile Asp His Thr Glu His Asp Val Met Val Ile Ser
            420                 425                 430

Glu Tyr Gly Tyr Ala Asp Leu Arg Gly Leu Ala Pro Arg Glu Arg Val
            435                 440                 445

Ala Lys Met Ile Gly Leu Ala His Pro Asp Tyr Arg Pro Leu Leu Glu
            450                 455                 460

Glu Tyr Tyr Ala Arg Ala Thr Ser Gly Asp Asn Lys Tyr Met Gln Thr
465                 470                 475                 480

Pro His Asp Leu Ala Thr Ala Phe Asp Phe His Ile Asn Leu Ala Lys
            485                 490                 495

Asn Gly Ser Met Lys Ala
            500

<210> SEQ ID NO 10
<211> LENGTH: 1140
<212> TYPE: PRT
<213> ORGANISM: Corynebacterium Glutamicum
<220> FEATURE:
<221> NAME/KEY: MISC FEATURE
<222> LOCATION: (1)..(1140)
<223> OTHER INFORMATION: ATCC13032

<400> SEQUENCE: 10

| | | | | | | | | | | | |
|---|---|---|---|---|---|---|---|---|---|---|---|
|Val|Ser|Thr|His|Thr|Ser|Thr|Leu|Pro|Ala|Phe|Lys|Lys|Ile|Leu
1||||5||||10||||15

Val Ala Asn Arg Gly Glu Ile Ala Val Arg Ala Phe Arg Ala Ala Leu
　　　　　20　　　　　　　　25　　　　　　　　30

Glu Thr Gly Ala Ala Thr Val Ala Ile Tyr Pro Arg Glu Asp Arg Gly
　　　　35　　　　　　　　40　　　　　　　　45

Ser Phe His Arg Ser Phe Ala Ser Glu Ala Val Arg Ile Gly Thr Glu
　　　50　　　　　　　　55　　　　　　　　60

Gly Ser Pro Val Lys Ala Tyr Leu Asp Ile Asp Glu Ile Ile Gly Ala
65　　　　　　　　70　　　　　　　　75　　　　　　　　80

Ala Lys Lys Val Lys Ala Asp Ala Ile Tyr Pro Gly Tyr Gly Phe Leu
　　　　　　　　85　　　　　　　　90　　　　　　　　95

Ser Glu Asn Ala Gln Leu Ala Arg Glu Cys Ala Glu Asn Gly Ile Thr
　　　　　　100　　　　　　　　105　　　　　　　　110

Phe Ile Gly Pro Thr Pro Glu Val Leu Asp Leu Thr Gly Asp Lys Ser
　　　　　115　　　　　　　　120　　　　　　　　125

Arg Ala Val Thr Ala Ala Lys Lys Ala Gly Leu Pro Val Leu Ala Glu
130　　　　　　　　135　　　　　　　　140

Ser Thr Pro Ser Lys Asn Ile Asp Glu Ile Val Lys Ser Ala Glu Gly
145　　　　　　　　150　　　　　　　　155　　　　　　　　160

Gln Thr Tyr Pro Ile Phe Val Lys Ala Val Ala Gly Gly Gly Gly Arg
　　　　　　　　165　　　　　　　　170　　　　　　　　175

Gly Met Arg Phe Val Ala Ser Pro Asp Glu Leu Arg Lys Leu Ala Thr
　　　　　180　　　　　　　　185　　　　　　　　190

Glu Ala Ser Arg Glu Ala Glu Ala Phe Gly Asp Gly Ala Val Tyr
　　　　　195　　　　　　　　200　　　　　　　　205

Val Glu Arg Ala Val Ile Asn Pro Gln His Ile Glu Val Gln Ile Leu
　　　　210　　　　　　　　215　　　　　　　　220

Gly Asp His Thr Gly Glu Val Val His Leu Tyr Glu Arg Asp Cys Ser
225　　　　　　　　230　　　　　　　　235　　　　　　　　240

Leu Gln Arg Arg His Gln Lys Val Val Glu Ile Ala Pro Ala Gln His
　　　　　　　　245　　　　　　　　250　　　　　　　　255

Leu Asp Pro Glu Leu Arg Asp Arg Ile Cys Ala Asp Ala Val Lys Phe
　　　　　　260　　　　　　　　265　　　　　　　　270

Cys Arg Ser Ile Gly Tyr Gln Gly Ala Gly Thr Val Glu Phe Leu Val
　　　　　275　　　　　　　　280　　　　　　　　285

Asp Glu Lys Gly Asn His Val Phe Ile Glu Met Asn Pro Arg Ile Gln
　　　　290　　　　　　　　295　　　　　　　　300

Val Glu His Thr Val Thr Glu Glu Val Thr Glu Val Asp Leu Val Lys
305　　　　　　　　310　　　　　　　　315　　　　　　　　320

Ala Gln Met Arg Leu Ala Ala Gly Ala Thr Leu Lys Glu Leu Gly Leu
　　　　　　　　325　　　　　　　　330　　　　　　　　335

Thr Gln Asp Lys Ile Lys Thr His Gly Ala Ala Leu Gln Cys Arg Ile
　　　　　　340　　　　　　　　345　　　　　　　　350

Thr Thr Glu Asp Pro Asn Asn Gly Phe Arg Pro Asp Thr Gly Thr Ile
　　　　　355　　　　　　　　360　　　　　　　　365

Thr Ala Tyr Arg Ser Pro Gly Gly Ala Gly Val Arg Leu Asp Gly Ala
　　　　370　　　　　　　　375　　　　　　　　380

Ala Gln Leu Gly Gly Glu Ile Thr Ala His Phe Asp Ser Met Leu Val
385　　　　　　　　390　　　　　　　　395　　　　　　　　400

Lys Met Thr Cys Arg Gly Ser Asp Phe Glu Thr Ala Val Ala Arg Ala

```
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
            435                 440                 445
Ile Ala Thr Gly Phe Ile Ala Asp His Pro His Leu Leu Gln Ala Pro
450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
            485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
            515                 520                 525
Arg Glu Gln Asp Ala Leu Ala Val Thr Asp Thr Thr Phe Arg Asp Ala
            530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
            595                 600                 605
Asn Ile Gln Met Leu Leu Arg Gly Arg Asn Thr Val Gly Tyr Thr Pro
            610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
            675                 680                 685
Leu Tyr Thr Leu Asp Tyr Tyr Leu Lys Met Ala Glu Glu Ile Val Lys
            690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
                725                 730                 735
Leu Pro Val His Val His Thr His Asp Thr Ala Gly Gly Gln Leu Ala
            740                 745                 750
Thr Tyr Phe Ala Ala Gln Ala Gly Ala Asp Ala Val Asp Gly Ala
            755                 760                 765
Ser Ala Pro Leu Ser Gly Thr Thr Ser Gln Pro Ser Leu Ser Ala Ile
            770                 775                 780
Val Ala Ala Phe Ala His Thr Arg Arg Asp Thr Gly Leu Ser Leu Glu
785                 790                 795                 800
Ala Val Ser Asp Leu Glu Pro Tyr Trp Glu Ala Val Arg Gly Leu Tyr
                805                 810                 815
Leu Pro Phe Glu Ser Gly Thr Pro Gly Pro Thr Gly Arg Val Tyr Arg
            820                 825                 830
```

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val Arg
    1010                1015                1020

Leu Asp Ala Ile Ser Glu Pro Asp Lys Gly Met Arg Asn Val Val
1025                1030                1035                1040

Ala Asn Val Asn Gly Gln Ile Arg Pro Met Arg Val Arg Asp Arg Ser
                1045                1050                1055

Val Glu Ser Val Thr Ala Thr Ala Glu Lys Ala Asp Ser Ser Asn Lys
            1060                1065                1070

Gly His Val Ala Ala Pro Phe Ala Gly Val Val Thr Val Thr Val Ala
        1075                1080                1085

Glu Gly Asp Glu Val Lys Ala Gly Asp Ala Val Ala Ile Ile Glu Ala
    1090                1095                1100

Met Lys Met Glu Ala Thr Ile Thr Ala Ser Val Asp Gly Lys Ile Asp
1105                1110                1115                1120

Arg Val Val Val Pro Ala Ala Thr Lys Val Glu Gly Gly Asp Leu Ile
                1125                1130                1135

Val Val Val Ser
        1140

<210> SEQ ID NO 11
<211> LENGTH: 35
<212> TYPE: DNA
<213> ORGANISM: Artificial Sequence
<220> FEATURE:
<223> OTHER INFORMATION: Synthetic primer ldhA_5_HindIII

<400> SEQUENCE: 11
ttttaagctt cgtcattgtt gccgaaaccg tggtg                              35

<210> SEQ ID NO 12
<211> LENGTH: 46
<212> TYPE: DNA
<213> ORGANISM: Artificial Sequence
<220> FEATURE:

<223> OTHER INFORMATION: Synthetic primer ldhA_up_3_XhoI

<400> SEQUENCE: 12
taggcgccaa agattctcga gtttcgatcc cacttcctga tttccc       46

<210> SEQ ID NO 13
<211> LENGTH: 48
<212> TYPE: DNA
<213> ORGANISM: Artificial Sequence
<220> FEATURE:
<223> OTHER INFORMATION: Synthetic primer ldhA_dn_5_XhoI

<400> SEQUENCE: 13
ggaagtggga tcgaaactcg agaatctttg gcgcctagtt ggcgacgc     48

<210> SEQ ID NO 14
<211> LENGTH: 35
<212> TYPE: DNA
<213> ORGANISM: Artificial Sequence
<220> FEATURE:
<223> OTHER INFORMATION: Synthetic primer ldhA_3_EcoRI

<400> SEQUENCE: 14
ttttgaattc ctcatcggca tcttcgaagg catcg                   35

<210> SEQ ID NO 15
<211> LENGTH: 42
<212> TYPE: DNA
<213> ORGANISM: Artificial Sequence
<220> FEATURE:
<223> OTHER INFORMATION: Synthetic primer poxB 5_H3

<400> SEQUENCE: 15
catgattacg ccaagctttc agcgtgggtc gggttctttg ag           42

<210> SEQ ID NO 16
<211> LENGTH: 32
<212> TYPE: DNA
<213> ORGANISM: Artificial Sequence
<220> FEATURE:
<223> OTHER INFORMATION: Synthetic primer DpoxB_up 3

<400> SEQUENCE: 16
aatcatcatc tgaactcctc aacgttatgg ct                      32

<210> SEQ ID NO 17
<211> LENGTH: 37
<212> TYPE: DNA
<213> ORGANISM: Artificial Sequence
<220> FEATURE:
<223> OTHER INFORMATION: Synthetic primer DpoxB_dn 5

<400> SEQUENCE: 17
ggagttcaga tgatgattga tacacctgct gttctca                 37

<210> SEQ ID NO 18
<211> LENGTH: 44
<212> TYPE: DNA
<213> ORGANISM: Artificial Sequence
<220> FEATURE:
<223> OTHER INFORMATION: Synthetic primer poxB 3 E1

<400> SEQUENCE: 18
acgacggcca gtgaattcat gtcccgaatc cacttcaatc agag         44

-continued

```
<210> SEQ ID NO 19
<211> LENGTH: 44
<212> TYPE: DNA
<213> ORGANISM: Artificial Sequence
<220> FEATURE:
<223> OTHER INFORMATION: Synthetic primer pta 5 H3

<400> SEQUENCE: 19
catgattacg ccaagcttcc ctccatgata cgtggtaagt gcag            44

<210> SEQ ID NO 20
<211> LENGTH: 43
<212> TYPE: DNA
<213> ORGANISM: Artificial Sequence
<220> FEATURE:
<223> OTHER INFORMATION: Synthetic primer Dpta_up_R1 3

<400> SEQUENCE: 20
gttccctgtt aatgtaacca gctgaggtcg gtgtgtcaga cat             43

<210> SEQ ID NO 21
<211> LENGTH: 48
<212> TYPE: DNA
<213> ORGANISM: Artificial Sequence
<220> FEATURE:
<223> OTHER INFORMATION: Synthetic primer DackA_dn_R1 5

<400> SEQUENCE: 21
ttacattaac agggaaccgg aagagttagc tatcgctagg tacgcggt        48

<210> SEQ ID NO 22
<211> LENGTH: 40
<212> TYPE: DNA
<213> ORGANISM: Artificial Sequence
<220> FEATURE:
<223> OTHER INFORMATION: Synthetic primer ackA 3 Xb

<400> SEQUENCE: 22
acccggggat cctctagagg gctgatgtga tttctgcggg                 40

<210> SEQ ID NO 23
<211> LENGTH: 41
<212> TYPE: DNA
<213> ORGANISM: Artificial Sequence
<220> FEATURE:
<223> OTHER INFORMATION: Synthetic primer actA 5 Xb

<400> SEQUENCE: 23
ggtggcggcc gctctagagg tctgagcttt attcctgggc t               41

<210> SEQ ID NO 24
<211> LENGTH: 36
<212> TYPE: DNA
<213> ORGANISM: Artificial Sequence
<220> FEATURE:
<223> OTHER INFORMATION: Synthetic primer DactA_up_R4 3

<400> SEQUENCE: 24
tctggataga agcatctaag ccagcgccgg tgaagc                     36

<210> SEQ ID NO 25
<211> LENGTH: 46
<212> TYPE: DNA
<213> ORGANISM: Artificial Sequence
<220> FEATURE:
<223> OTHER INFORMATION: Synthetic primer DactA_dn_R4 5
```

<400> SEQUENCE: 25
agatgcttct atccagagct ccggtgacaa caagtacatg cagacc                46

<210> SEQ ID NO 26
<211> LENGTH: 39
<212> TYPE: DNA
<213> ORGANISM: Artificial Sequence
<220> FEATURE:
<223> OTHER INFORMATION: Synthetic primer actA 3 H3

<400> SEQUENCE: 26
gacggtatcg ataagcttcg tacgatgctt gagcggtat                        39

<210> SEQ ID NO 27
<211> LENGTH: 44
<212> TYPE: DNA
<213> ORGANISM: Artificial Sequence
<220> FEATURE:
<223> OTHER INFORMATION: Synthetic primer pyc-F1

<400> SEQUENCE: 27
catgattacg ccaagcttga ttactgaagc agcacgtcag ctgg                  44

<210> SEQ ID NO 28
<211> LENGTH: 36
<212> TYPE: DNA
<213> ORGANISM: Artificial Sequence
<220> FEATURE:
<223> OTHER INFORMATION: Synthetic primer pyc-R1

<400> SEQUENCE: 28
gagcaggtgg gagtggtctg caatgaatcc ggtggc                           36

<210> SEQ ID NO 29
<211> LENGTH: 34
<212> TYPE: DNA
<213> ORGANISM: Artificial Sequence
<220> FEATURE:
<223> OTHER INFORMATION: Synthetic primer pyc-F2

<400> SEQUENCE: 29
agaccactcc cacctgctcc aggctccacc tgct                             34

<210> SEQ ID NO 30
<211> LENGTH: 42
<212> TYPE: DNA
<213> ORGANISM: Artificial Sequence
<220> FEATURE:
<223> OTHER INFORMATION: Synthetic primer pyc-R2

<400> SEQUENCE: 30
acgacggcca gtgaattcca ccggtgagat caagaacctc tg                    42

<210> SEQ ID NO 31
<211> LENGTH: 19
<212> TYPE: DNA
<213> ORGANISM: Artificial Sequence
<220> FEATURE:
<223> OTHER INFORMATION: Synthetic primer poxB_up_for

<400> SEQUENCE: 31
ggctgaaacc aaaccagac                                              19

<210> SEQ ID NO 32
<211> LENGTH: 22

```
<212> TYPE: DNA
<213> ORGANISM: Artificial Sequence
<220> FEATURE:
<223> OTHER INFORMATION: Synthetic primer poxB_dn_rev

<400> SEQUENCE: 32
ctgcatgatc ggttagatac ag                                          22

<210> SEQ ID NO 33
<211> LENGTH: 18
<212> TYPE: DNA
<213> ORGANISM: Artificial Sequence
<220> FEATURE:
<223> OTHER INFORMATION: Synthetic primer pta_up_for

<400> SEQUENCE: 33
gcgtggaatt gagatcgg                                               18

<210> SEQ ID NO 34
<211> LENGTH: 18
<212> TYPE: DNA
<213> ORGANISM: Artificial Sequence
<220> FEATURE:
<223> OTHER INFORMATION: Synthetic primer ackA_dn_rev

<400> SEQUENCE: 34
cagagcgatt tgtggtgg                                               18

<210> SEQ ID NO 35
<211> LENGTH: 20
<212> TYPE: DNA
<213> ORGANISM: Artificial Sequence
<220> FEATURE:
<223> OTHER INFORMATION: Synthetic primer actA_up_for

<400> SEQUENCE: 35
tgaagcaatg gtgtgaactg                                             20

<210> SEQ ID NO 36
<211> LENGTH: 19
<212> TYPE: DNA
<213> ORGANISM: Artificial Sequence
<220> FEATURE:
<223> OTHER INFORMATION: Synthetic primer actA_dn_rev

<400> SEQUENCE: 36
gctaccaaac actagcctg                                              19

<210> SEQ ID NO 37
<211> LENGTH: 32
<212> TYPE: DNA
<213> ORGANISM: Artificial Sequence
<220> FEATURE:
<223> OTHER INFORMATION: Synthetic primer Tuf-F

<400> SEQUENCE: 37
tagggcgaat tgggtacaca gtaggcgcgt ag                               32

<210> SEQ ID NO 38
<211> LENGTH: 32
<212> TYPE: DNA
<213> ORGANISM: Artificial Sequence
<220> FEATURE:
<223> OTHER INFORMATION: Synthetic primer Tuf-R

<400> SEQUENCE: 38
```

```
cgagggggc ccggtaccgg ttgtcctcct tt                              32
```

<210> SEQ ID NO 39
<211> LENGTH: 33
<212> TYPE: DNA
<213> ORGANISM: Artificial Sequence
<220> FEATURE:
<223> OTHER INFORMATION: Synthetic primer for glnDK amplification

<400> SEQUENCE: 39

```
ttttaagctt tcttttgaa ggagacgatc atg                             33
```

<210> SEQ ID NO 40
<211> LENGTH: 28
<212> TYPE: DNA
<213> ORGANISM: Artificial Sequence
<220> FEATURE:
<223> OTHER INFORMATION: Synthetic primer for glnDK amplification

<400> SEQUENCE: 40

```
ttttgaattc agctacctgc caacgacc                                  28
```

<210> SEQ ID NO 41
<211> LENGTH: 45
<212> TYPE: DNA
<213> ORGANISM: Artificial Sequence
<220> FEATURE:
<223> OTHER INFORMATION: Synthetic primer for glnD amplification

<400> SEQUENCE: 41

```
ttttaagctt aaaggaggac aaccatgaat aatccagccc agctg                45
```

<210> SEQ ID NO 42
<211> LENGTH: 5342
<212> TYPE: DNA
<213> ORGANISM: Artificial Sequence
<220> FEATURE:
<223> OTHER INFORMATION: Synthetic pGT1 vector nucleotide sequence

<400> SEQUENCE: 42

```
ttgagatcct ttttttctgc gcgtaatctg ctgcttgcaa acaaaaaaac caccgctacc    60
agcggtggtt tgtttgccgg atcaagagct accaactctt tttccgaagg taactggctt   120
cagcagagcg cagataccaa atactgttct tctagtgtag ccgtagttag gccaccactt   180
caagaactct gtagcaccgc ctacatacct cgctctgcta atcctgttac cagtggctgc   240
tgccagtggc gataagtcgt gtcttaccgg gttggactca agacgatagt taccggataa   300
ggcgcagcgg tcgggctgaa cggggggttc gtgcacacag cccagcttgg agcgaacgac   360
ctacaccgaa ctgagatacc tacagcgtga gctatgagaa agcgccacgc ttcccgaagg   420
gagaaaggcg gacaggtatc cggtaagcgg cagggtcgga acaggagagc gcacgaggga   480
gcttccaggg ggaaacgcct ggtatcttta gtcctgtc gggtttcgcc acctctgact    540
tgagcgtcga ttttgtgat gctcgtcagg ggggcggagc ctatgaaaa acgccctct    600
tcgctattac gccagctggc aaagggga tgtgctgcaa ggcgattaag ttgggtaacg   660
ccagggtttt cccagtcacg acgttgtaaa acgacggcca gtgaattgta atacgactca   720
ctataggggcg aattgggtac cgggccccc ctcgaggtcg acggtatcga taagcttgat   780
atcgaattcc tgcagcccgg ggatccact agttctagag cggccgccac cgcggtggag   840
ctcatttagc ggatgattct cgttcaactt cggccgaagc cacttcgtct gtcataatga   900
caggatggt tcggccgtt tttgcaaata aaacgaaagg ctcagtcgaa agactgggcc   960
```

```
tttcgtttta tctgttgttt gtcggtgaac gctctcctga gtaggacaaa tccgccggga   1020
gcggatttga acgttgcgaa gcaacggccc ggagggtggc gggcaggacg cccgccataa   1080
actgccaggc atcaaattaa gcagaaggcc atcctgacgg atggccttt tgcgtttcta    1140 caaactcttc ctgtcgtcat atctacaagc catcccccca cagatacggt agctccagct   1200
tttgttccct ttagtgaggg ttaatttcga gcttggcgta atcatggtca tagctgtttc   1260
ctgtgtgaaa ttgttatccg ctcacaattc cacacaacat acgagccgga agcataaagt   1320
gtaaagcctg ggaacaacaa gacccatcat agtttgcccc cgcgacattg accataaatt   1380
catcgcacaa aatatcgaac ggggtttatg ccgcttttag tgggtgcgaa gaatagtctg   1440
ctcattaccc gcgaacaccg ccgcattcag atcacgctta gtagcgtccc catgagtagg   1500
cagaaccgcg tccaagtcca catcatccat aacgatcatg cacggggtgg aatccacacc   1560
cagacttgcc agcacctcat tagcgacacg ttgcgcagcg gccacgtcct tagccttatc   1620
cacgcaatct aggacgtact gcctaaccgc gaaatcagac tgaatcagtt tccaatcatc   1680
gggcttcacc aaagcaacag caacgcgggt tgattcgacc cgttccggtg cttccagacc   1740
ggcgagcttg tacagttctt cttccatttc acgacgtaca tcagcgtcta tgtaatcaat   1800
gcccaaagca cgcttagccc cacgtgacca ggacgaacgc aggtttttag aaccaacctc   1860
atactcacgc caccgagcca ccaaaacagc gtccatatcc tcgccggcgt cgctttgatc   1920
ggccaacata tccaacatct gaaacggcgt gtacgacccc ttagacgcgg ttttagtagc   1980
ggagccagtc agttcctgag acatgccctt agcgaggtag gttgccattt tcgcagcgtc   2040
tccaccccag gtagacacct gatcaagttt gaccccgtgc tcacgcagtg gcgcgtccat   2100
accggcctta accacaccag cagaccagcg ggaaaacatg gaatcctcaa acgccttgag   2160
ttcatcgtca gacagtggac gatccaagaa caacagcatg ttgcggtgca agtgccaacc   2220
gttcgcccaa gagtctgtga cctcatagtc actataggtg tgctccaccc cgtaccgtgc   2280
acgttctttc ttccactgag atgttttcac catcgaagag tacgcagtct taatacccgc   2340
ttcaacctgc gcaaatgact gtgagcggtt gtgtcgaaca gtgccacaa acatcatgag    2400 cgcgccaccc gccgccaagt gattcttagt agcaatagcc agctcaatgc ggcgttcgcc   2460
catgacttcc aattcagcca gaggtgaccc ccagcgagag tgagagtttt gcagaccctc   2520
aaactgcgaa gcaccgttag acgaccagga caccgcaaca gcttcgtccc tgcgccacct   2580
atggcacccc gccagagcct tactattggt gatcttgtac atgacgtttt gcctacgcca   2640
cgccctagcg cgagtgacct tagaaccctc attgacctgc ggttccttag aggtgttcac   2700
ttctatttca gtgttaccta gacccgatgt tgtgcggggt tgcgcagtgc gagtttgtgc   2760
gggtgttgtg cccgttgtct tagctagtgc tatggttgtc aattgaaacc ccttcgggtt   2820
atgtggcccc cgtgcatatg agttggtagc tcgcacgggg gtttgtcttg tctaggaact   2880
attaattttt agtggtgttt ggtggccgcc tagcttggct atgcgtgcca gcttacccgt   2940
actcaatgtt aaagatttgc atcgacatgg gagggttacg tgtccgatac ctagggggg    3000 tatccgcgac taggtgcccc ggtgctcact gtctgtaccg gcggggcaag ccccacaccc   3060
cgcatggaca gggtggctcc gccccctgca cccccagcaa tctgcatgta catgtttac    3120 acattagcac gacatgactg catgtgcatg cactgcatgc agactaggta aatatgagta   3180
tgtacgacta gtaacaggag cactgcacat aatgaatgag ttgcaggaca atgtttgcta   3240
cgcatgcgca tgacatatcg caggaaagct actagagtct taaagcatgg caaccaaggc   3300
```

```
acagctagaa cagcaactac aagaagctca acaggcacta caggcgcagc aagcgcaggc    3360
acaagccacc atcgaagcac tagaagcgca ggcaaaggct aagcccgtcg tggtcaccgc    3420
acgcgttcct ttggcactac gtgaggacat gaagcgcgca ggcatgcaga acggtgaaaa    3480
cctccaagag ttcatgatcg ccgcgtttac cgagcggcta gaaaagctca ccaccaccga    3540
caacgaggaa aacaatgtct aacccactag ttctctttgc ccaccgtgac ccggtaaatg    3600
acgtgacgtt cgagtgcatt gagcacgcca cctacgacac actttcacac gctaaagacc    3660
agatcaccgc ccaaatgcaa gccctagacg aagaagccgc cctactgccc taatgggtgt    3720
ttcatgggtg tttccctagt gtttcatggt gttttcacct aagctaggga attgcgcgag    3780
aagtctcgca aaaatcagca accccggaa ccacacagtt cacgggggtt cttctatgcc    3840
agaaatcaga aaggggaacc agtgaacgac cccgaatatt ggatcacagc gcagcaggtc    3900
gccgcccgcg tagctctcac cccggccacc attaaaaagt gggcaaacga gggaaaaatc    3960
accgcataca agatcggcaa gtccgtccga ttcaaagcat cagacgtaga caagctaggg    4020
gggggggggc gctgaggtct gcctcgtgaa gaaggtgttg ctgactcata ccaggcctga    4080
atcgccccat catccagcca gaaagtgagg gagccacggt tgatgagagc tttgttgtag    4140
gtggaccagt tggtgatttt gaacttttgc tttgccacgg aacggtctgc gttgtcggga    4200
agatgcgtga tctgatcctt caactcagca aaagttcgat ttattcaaca aagccgccgt    4260
cccgtcaagt cagcgtaatg ctctgccagt gttacaacca attaaccaat tctgattaga    4320
agaactcgtc aagaaggcga tagaaggcga tgcgctgcga atcgggagcg gcgataccgt    4380
aaagcacgag gaagcggtca gcccattcgc cgccaagctc ttcagcaata tcacgggtag    4440
ccaacgctat gtcctgatag cggtccgcca cacccagccg gccacagtcg atgaatccag    4500
aaaagcggcc attttccacc atgatattcg gcaagcaggc atcgccatgg gtcacgacga    4560
gatcctcgcc gtcgggcatg ctcgccttga gcctggcgaa cagttcggct ggcgcgagcc    4620
cctgatgctc ttcgtccaga tcatcctgat cgacaagacc ggcttccatc cgagtacgtg    4680
ctcgctcgat gcgatgtttc gcttggtggt cgaatgggca ggtagccgga tcaagcgtat    4740
gcagccgccg cattgcatca gccatgatgg atactttctc ggcaggagca aggtgagatg    4800
acaggagatc ctgccccggc acttcgccca atagcagcca gtcccttccc gcttcagtga    4860
caacgtcgag cacagctgcg caaggaacgc ccgtcgtggc cagccacgat agccgcgctg    4920
cctcgtcttg cagttcattc agggcaccgg acaggtcggt cttgacaaaa agaaccgggc    4980
gcccctgcgc tgacagccgg aacacggcgg catcagagca gccgattgtc tgttgtgccc    5040
agtcatagcc gaatagcctc tccacccaag cggccgagaa acctgcgtgc aatccatctt    5100
gttcaatcat aacacccctt gtattactgt ttatgtaagc agacagtttt attgttcatg    5160
atgatatatt tttatcttgt gcaatgtaac atcagagatt ttgagacaca acgtggcttt    5220
cccccccccc ccaaaaggat ctaggtgaag atccttttg ataatctcat gaccaaaatc    5280
ccttaacgtg agttttcgtt ccactgagcg tcagaccccg tagaaaagat caaggatct    5340 tc                                                                  5342
```